(12) United States Patent
Van Dyke

(10) Patent No.: US 6,911,454 B1
(45) Date of Patent: Jun. 28, 2005

(54) METHOD FOR POTENTIATING PRIMARY DRUGS IN TREATING MULTIDRUG RESISTANT DISEASE

(75) Inventor: Knox Van Dyke, Morgantown, WV (US)

(73) Assignee: Cancer Biologics of America, Inc., Lexington, KY (US)

(*) Notice: Subject to any disclaimer, the term of this patent is extended or adjusted under 35 U.S.C. 154(b) by 0 days.

(21) Appl. No.: 08/293,745

(22) Filed: Aug. 22, 1994

Related U.S. Application Data

(63) Continuation of application No. 07/973,627, filed on Nov. 9, 1992, now abandoned, which is a continuation-in-part of application No. 07/689,003, filed on Apr. 19, 1991, now abandoned, which is a continuation-in-part of application No. 07/537,349, filed on Jun. 13, 1990, now abandoned, and a continuation-in-part of application No. 07/413,710, filed on Sep. 28, 1989, now abandoned, which is a continuation-in-part of application No. 07/413,711, filed on Sep. 28, 1989, now Pat. No. 5,025,020.

(51) Int. Cl.[7] ............................................. A61K 31/47
(52) U.S. Cl. ...................................... 514/308; 514/309
(58) Field of Search ................................... 514/308, 309

(56) References Cited

U.S. PATENT DOCUMENTS 4,761,417 A * 8/1988 Maroko ....................... 514/784
5,079,363 A   1/1992 Bouisset et al. ............... 546/64
5,086,059 A   2/1992 Ardecky et al. ............. 514/284

FOREIGN PATENT DOCUMENTS

WO    9218131    10/1992

OTHER PUBLICATIONS

Liao 93CA: 197657u 1980.*
Fuska 104 CA: 84939–q 1985.*
Dept of Pharmacology et al, Chinese Medical Journal 93(3): pp 193–198 1979.*
Fang et al. "A new calcium Antagonist of Chinese Medical Oxygen Tetrandrine" Journal of Hypertension 1986 4(Supp 6) 5150–5152.*
Qian et al Hypotensive Activity of Tetrandrine in Pos Pharmacology 26:187–197 (1983).*
Kawashima et al General Pharmacology vol. 21 #3 pp 343–347 1990.*
Grolla et al Cornea Chemotherapy Reports Part 3 vol. 5 #1 Sep. 1974 pp 79–85.*
Griffiths, CA 99:133454s 1983.*
Akiyama, CA 108:161022y 1988.*
Kuroda, CA 86:65337k 1977.*
Mitscher, CA 75:59821v 1971.*
Merck Index 10th Ed # 2136 & 9050.*
Merck Index 10Ed 9056, 2136.*
CA # 86 202f Cerny et al 1977.*
CA # 86 65337k Kureida et al 1977.*
Merck Index 10th Ed #3436, 9784, 9788.*
Fournel et al 110:CA: 132057 1988.*
Fournel et al 110 CA 132058z 1988.*

(Continued)

Primary Examiner—Russell Travers
(74) Attorney, Agent, or Firm—Price, Heneveld, Cooper, DeWitt & Litton

(57) ABSTRACT

The specification discloses a method for enhancing the inhibiting action of drugs against multidrug resistant cells, apparently by reversing or inhibiting the glycoprotein "pumps" associated with such cells.

81 Claims, 8 Drawing Sheets

OTHER PUBLICATIONS

"Protein Kinase C Phosphorylates P–Glycoprotein in Multidrug Resistant Human KB Carcinoma Cells," by T.C. Chambers et al., The Journal of Biological Chemistry, vol. 265, No. 13, May 5, 1990, pp. 7679–7686.

"The Dependence of the Tuberculostatic Activity of Bis Benzyl Iso Quinoline Alkaloids on their Structure," Database Biosis Biosciences Information Service, & Farmatsiya, vol. 27, No. 2, 1978, pp. 23–26, O.N. Tolkachev et al. (Abstract).

"Chemotherapeutic Properties of the Alkaloid Tetrandrine in Experimental Tuberculosis," Database Chemabs Chemical Abstracts Service, & Farmakol. Toksikol., vol. 36, No. 1, 1973, pp. 74–78, S.A., Vichkanova et al. (Abstract), CA:78(17) 106079h.

"Tuberculostatic Activity of Preparations from Plants," by S.A. Vichkanova et al., Database Chemabs, Chemical Abstracts Service, & Fitontsidy, Mater. Soveshch., 6th Meeting, 1969, pp. 90–94. (abstract). CA78(11):66905R.

"Effects of Methoxyadiantifoline on Coronary Circulation and Contractility of Coronary Strips," by Jufang Jia et al., Database Chemabs, Chemical Abstracts Service, vol. 2, No. 3, 1988, pp. 193–196, (Abstract). CA109(19):163208g.

"Interaction of Bisbenzylisoquinoline Alkaloids with Alveolar Macrophages," by J.Y.C. Ma et al., Faseb J., vol. 4, No. 7, 1990, p. A2116, (Abstract).

"Effects of Bisbenzylisoquinoline Alkaloids on Alveolar Macrophages: Correlation Between Binding Affinity, Inhibitory Potency, and Antifibrotic Potential," by V. Castranova et al., Toxicology and Applied Pharmacology, vol. 108, No. 2, 1991, pp. 242–252.

"Selective Antimalarial Activity of Tetrandrine Against Chloroquine Resistant Plasmodium Falciparum," Biophysical and Biochemical Research Communications, vol. 159, No. 1, Feb. 28, 1989, pp. 242–248.

"The Potentiating Action of Tetrandrine in Combination with Chloroquine or Qinghaosu Against Chloroquine–Sensitive and Resistant Falciparum Malaria," Biochemical and Biophysical Research Communications, vol. 165, No. 2, Dec. 15, 1989, pp. 758–765. By Applicant.

"In Vitro Activity on Epimastigotes of Three Typified Strains of Trypanosoma Cruzi," Journal of Ethnopharmacology, 24 (1988) 337–343, A. Fournet et al.

"In Vitro Activity on the Promastigotes of Three Strains of Leishmania," Journal of Ethnopharmacology, 24 (1988) 327–335, A. Fournet et al.

Phosphorylation of the $M_r$ 170,000 to 180,000 Glycoprotein Specific to Multidrug–resistant Tumor Cells: Effects of Verapamil, Trifluorperazine, and Phorbol Esters[1], by Hamada et al., Cancer Research 47, 2860–2865, Jun. 1, 1987.

Overcoming Multidrug Resistance In Malaria, by Swyers, Research Resources Reporter, Feb. 1990, vol. XIV, No. 2.

9056. Tetrandrine, Merck Index, No. 9061, p. 1321.

84:159552n, 1–Pharmacodynamics, vol. 84, 1976, p. 17.

55716e, Chemical Abstracts, vol. 72, 1970, p. 464.

86:202t, Chemical Abstracts, vol. 86, 1977, p. 16.

106:135e, Chemical Abstracts, vol. 106, 1987, pp. 127–128.

108:87627e, 1–Pharmacology, vol. 108, 1988, p. 23.

110:132058z, Chemical Abstracts, vol. 110, 1989, p. 416.

What is Synergy?, by Berenbaum, The American Society for Pharmacology and Experimental Therapeutics, vol. 1989, No. 41, pp. 93–141.

Manual of Pharmacologic Calculations, by Tallarida et al., pp. 54–113.

$^3$H–Azidopine Photoaffinity Labeling of High Molecular Weight Proteins in Chloroquine Resistant Falciparum Malaria, by Ye et al., Biochemical and Biophysical Research Communications, vol. 162, No. 2, 1989, Jul. 31, 1989, pp. 809–813.

Genetic mapping of the chloroquine–resistance locus on Plasmodium falciparum chromosome 7, by Wellems et al., Proc. Natl. Acad. Sci. vol. 88, pp. 3382–3386, Apr. 1991.

Amplification of a Gene Related to Mammalian mdr Genes in Drug–Resistant Plasmodium falciparum, by Wilson et al., Science, vol. 24, pp. 1184–1186, 1989.

The Potentiating Action of Tetrandrine in Combination with Chloroquine or Qinghaosu Against Chloroquine–Sensitive and Resistant Falciparum Malaria, by Ye et al., Biochemical and Biophysical Research Communications, vol. 165, No. 2, 1989, Dec. 15, 1989, pp. 758–765.

Amplification of the Multidrug Resistance Gene in Some Chloroquine–Resistant Isolates of *P. falciparum*, by Foote et al., Cell, vol. 57, 921–930, Jun. 16, 1989.

Merck Index, 8th ed., p. 142.

6387. Nifurtimox, Merck Index, p. 938.

Mechanism of multidrug resistance, by Bradley et al., Biochimica et Biophysica Acta, 948 (1988) 87–128.

Immunohistochemical Analysis of P–glycoprotein Expression Correlated with Chemotherapy Resistance in Locally Advanced Breast Cancer, by Ro et al., Original Contributions, pp. 787–791.

Detection of Multidrug Resistance Associated P–170 Glycoprotein in Previously Untreated Non Small Cell Lung Cancer, by Scagliotti et al., Anticancer Research II:2207–2210 (1991).

Clinical Relevance of Immunohistochemical Detection of Multidrug Resistance P–glycoprotein in Breast Carcinoma, Reports, vol. 83, No. 2, Jan. 16, 1991, pp. 111–116.

Clinical Significance of Multidrug Resistance P–glycoprotein Expression on Acute Nonlymphoblastic Leukemia Cells at Diagnosis, by Campos et al., Blood, vol. 79, No. 2 (Jan. 15), 1992, pp. 473–476.

Detection of Multidrug Resistance Markers, P–glycoprotein and mdr1 mRNA, in Human Leukemia Cells, by Tsurno et al., Jpn. J. Cancer Res. (Gann), 78, 1415–1419, Dec. 1987.

Multidrug (Pleiotropic) Resistance in the Human Sarcoma Cell Line MES–SA, by Sikic, et al., Chapter 3, pp. 37–47.

Vichkanova, S.A.; Makarova, L.V.; Solov'eva, L.F., "Chemotherapeutic Properties of the Alkaloid"—Abstract CA78(17) 106079h 1973.

Vichkanova, S.A.; Makarova, L.V.; Gordeikina, N.I., "Tuberculostatic Activity of Preparations from Plants"— Abstract CA78(11)66905R 1972.

Tolkachev O.N.; Vichkanova, S.A.; Makarova L.V.; Naidovich L.P., "The Dependence of the Tuberculostatic Activity of Bis Benzyl Iso Quinoline Alkoids on their Structure"— Abstract 79:166230 Biosis 1979.

* cited by examiner

METHOD FOR POTENTIATING PRIMARY DRUGS IN TREATING MULTIDRUG RESISTANT DISEASE

CROSS-REFERENCE TO RELATED APPLICATION

This patent application is a continuation of application Ser. No. 07/973,627, filed Nov. 9, 1992, now abandoned which in turn is a continuation-in-part of U.S. patent application Ser. No. 07/689,003, filed Apr. 19, 1991, and entitled "METHOD FOR POTENTIATING PRIMARY DRUGS IN TREATING MULTIDRUG RESISTANT CELLS," which was abandoned effective on the filing of this application, and which is in turn a continuation-in-part of U.S. patent application Ser. No. 07/537,349, filed Jun. 13, 1990, and entitled "METHOD FOR TREATING MULTIDRUG RESISTANCE INFECTION," now abandoned, and is also a continuation-in-part of U.S. patent application Ser. No. 07/413,710, filed Sep. 28, 1989, and entitled "METHOD FOR POTENTIATING PRIMARY DRUGS IN TREATING MULTIDRUG RESISTANT CELLS," now abandoned, and is a continuation-in-part of U.S. patent application Ser. No. 07/413,711, filed Sep. 28, 1989, and enttitled "USE OF TETRANDRINE AND ITS DERIVATIVES TO TREAT MALARIA," now U.S. Pat. No. 5,025,020.

BACKGROUND OF THE INVENTION

Multidrug resistance is a phenomenon which has been observed in cancer and in a number of parasitic disease such as malaria, tuberculosis, Entamoeba histolytica (amoebic dysentery), Trypanosoma (African sleeping sickness), Leishmania and AIDS pneumonia.

A number of diverse drugs have been found effective against such diseases. However in many cases, the initial success of physicians in treating the disease is followed by total failure. Drugs which worked initially become totally ineffective after a period of time. An initial period of remission is often followed by a period of frustration during which nothing seems to be effective against the disease. Death becomes inevitable.

Such multidrug resistance in cancer cells has been associated with an increase in the drug resistant cell of the presence of 150,000 to 170,000 molecular weight glycoproteins. Such P150-170 Kd glycoproteins act as a drug exit pump, to pump disease fighting drugs out of the infected or infecting cells which the drugs are supposed to kill. This glycoprotein pump phenomenon in cancer cells has been reported in a March 1989 *Scientific American* article by Kartner and Ling. (No concession is made that this publication is prior art as to subject matter contained in the parent applications.) The presence of a very similar glycoprotein pump in drug resistant malaria has also been discovered by the inventor.

It has been reported by Rothenberg and Ling that multi-drug resistance in cancer can be reversed by using hydrophobic molecules with two planar aromatic rings and a tertiary basic nitrogen atom with a positive charge at physiologic pH. *Journal of the National Cancer Institute*, Vol. 81, No. 12, Jun. 21, 1989, on page 907. (No concession is made that this publication is prior art as to subject matter contained in the parent applications.) A representative compound of this class, and indeed apparently a member of this class which has actually been the subject of much experimental work is the drug verapamil, whose structural formula is shown below:

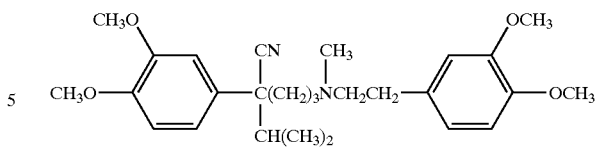

Verapamil is a calcium channel blocker. Other researchers have claimed that calcium channel blockers are effective against malaria. However while such results may be substantiatable in vitro, they have little practical value as clinical treatments in vivo. While calcium channel blockers are therapeutic in the treatment of hypertension at moderate levels, they are toxic at levels high enough to effect MDR reversal.

Another technique for MDR reversal in cancer which is of laboratory interest but which has no practical applicability involves inducing point mutations of the energy related ATP binding sites in the glycoprotein. Such point mutations result in an almost complete loss of MDR activity, according to Rothenberg and Ling, supra. While such in vitro work is important, it lacks in vivo clinical applicability.

Shiraishi et al. disclose in vitro work on the use of cepharanthine to treat multidrug resistance in cancer. Isotetrandrine, d-tetrandrine, fangchinoline and berbamine are said to show similar effects in cancer. Anti-tumor effects of d-tetrandrine have also been mentioned.

Heretofore, the phenomenon of multidrug resistance in such disease cells have been attributed to the presence of naturally occurring P150-170 Kd glycoproteins in the disease cells. It is believed that when the disease colony is exposed to treatment, the cells with the glycoprotein, or with a higher percentage thereof, survive the initial treatment while cells without glycoprotein, or with a lesser concentration thereof, do not. The surviving remnant then reproduces and eventually creates a colony which is substantially if not totally resistant to treatment with any drug.

A recent publication in the *Proceedings of the National Academy of Science*, reveals that multidrug resistance can also be caused by viral infection. "A retrovirus carrying an MDR1 cDNA confers multidrug resistance and polarized expression of P-glycoprotein in MDCK cells," *Proc. Natl. Acad. Sci. USA*, Ira Pastan et al., Vol. 85, pages 4486–4490, June 1988, Medical Sciences. The authors inserted a full-length cDNA for the human multidrug resistance gene (MDR1) into a retroviral vector. They were able to infect cells with this virus so that the cells expressed P-glycoprotein and rendered the cell multidrug resistant.

This experimental work raises the specter of multidrug resistant infection through accidental release of such manufactured retrovirus. Perhaps more significantly, it suggests the possible natural occurrence of retrovirus carrying such cDNA.

The implications of these possibilities are that diseases normally treatable with drugs initially, including cancers, may become untreatable ab initio due to infection with such multidrug resistance carrying virus. Such virus could through natural or artificial means infect body cells which may later become cancerous, or could infect the cells of parasitic diseases such as malaria, tuberculosis, AIDS pneumonia, African sleeping sickness and other such diseases. The presence of sizable colonies of such multidrug resistant disease cells would render the diseases and cancers particularly aggressive and virulent and very possibly baffling to an unsuspecting physician.

Researchers throughout the world continue to press for techniques for reversing multidrug resistance. A successful clinical technique for reversing multidrug resistance will be one of the most important breakthroughs in the fight against cancer, malaria, tuberculosis and other diseases exhibiting the multidrug resistance phenomenon.

SUMMARY OF THE INVENTION

In the present invention it has been surprisingly found that d-tetrandrine and certain of its derivatives act not only to reverse multidrug resistance but also to potentiate the effectiveness of a primary drug against a drug resistant cancer. The method of the present invention appears to reverse or inhibit the glycoprotein pump of a multidrug resistant cell so that such a resistant cell actually accepts a greater concentration of drug than a so-called drug resistant cell.

These surprising and unexpected results, as well as other objects, advantages and features of the present invention will be more fully understood and appreciated by reference to the Description of the Preferred Embodiment and appended drawings.

DESCRIPTION OF THE PREFERRED EMBODIMENT

Figure 1:
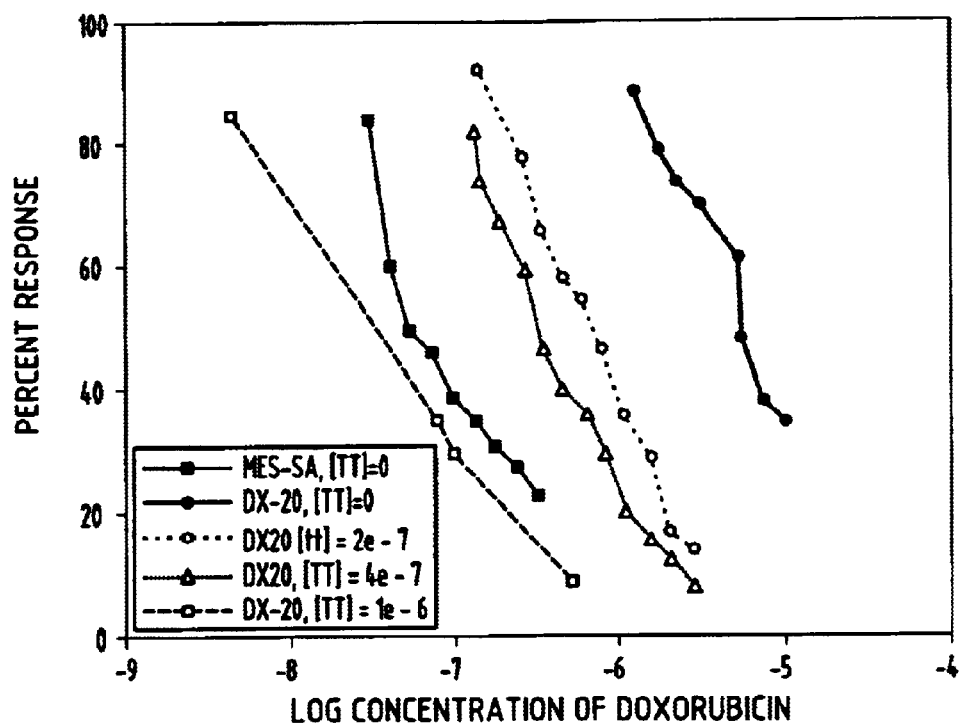
FIG. 1 is a graph comparing different concentrations of doxorubicin (adriamycin) and d-tetrandrine alone and in combination when used against DX20 to parent MES-SA cells.

In the preferred embodiment, the d-tetrandrine like compounds of the present invention have the following structural formula:

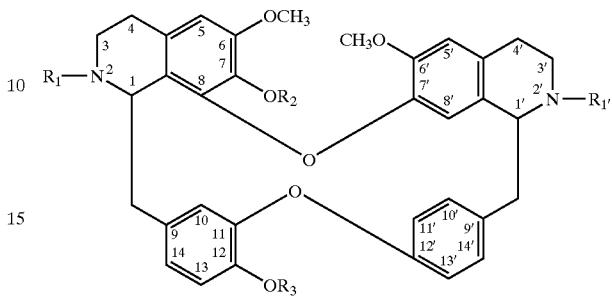

where $R_1$ and $R_1'$ are the same or different shortchained carbon based ligand including without limitation, $CH_3$, $CO_2CH_3$ or H; and $R_2$ is $CH_3$ or $C_2H_5$; and $R_3$ is $CH_3$ or hydrogen; and where the chemical structure has the "S" isomeric configuration at the C-1' chiral carbon location.

The d-tetrandrine family of compounds as a whole includes d-tetrandrine, isotetrandrine, hernandezine, berbamine, pycnamine, phaeanthine, obamegine, ethyl fangchinoline and fangchinoline, which list is not intended to be exhaustive. In all of these examples, $R_1$ and $R_1'$ constitute the methyl group. Variation within the group occurs in that $R_2$ and $R_3$ may constitute either a methyl group or hydrogen, and the isomeric configuration of the compounds at the C-1 and C-1' chiral carbon positions is either R (rectus) or S (sinister). The rules for R and S configuration can be found in Morrison and Boyd, "Organic Chemistry," 4th Edition, copyright 1983 by Allyn and Bacon, at pages 138–141. In addition, hernandezine includes a methoxy group at the C-5 position, a substitution which does not appear to be significant in the operability of the compound in the present invention. The specific manner in which these exemplary family members vary is set forth in Table VII below, wherein these family members are compared to two nonfamily members for activity against drug sensitive and drug resistant strains of P. falciparum malaria.

Not all members of the d-tetrandrine family of compounds operate to enhance or potentiate the activity of a primary drug against a multidrug resistant cell. Only those members of the family having the specific configuration outlined above are operable in this manner. Of the representative members of the family above, only d-tetrandrine, isotetrandrine, hernandezine, ethyl fangchinoline and berbamine appear to potentiate the primary drug against multidrug resistant cells.

In addition to these specific members of the d-tetrandrine family, it has been found that methoxadiantifoline also potentiates the effectiveness of a primary drug against a multidrug resistant cell. These compounds actually make the drug resistant cell more sensitive to the inhibitory action of a drug than is the so-called drug sensitive cell. At present, the only logical explanation for this result is that the method of the present invention actually involves reversing the glycoprotein pumps which are found in greater abundance on drug resistant cells. Another explanation is that multidrug resistant cells are actually more sensitive than drug sensitive cells to the primary toxic drug but this cannot be seen until the exit pump is inhibited. Thus the glycoprotein pump mechanism which originally made the cell multidrug resistant to drug inhibition actually works against the cell in the present invention to make the cell more sensitive to drug inhibition.

A specific in vivo dosage for each of the various compounds used in the present invention has not been established. However, such dosage can be established through routine clinical experimentation by referencing the concentrations at which the various compounds have exhibited 50% inhibition as set forth in the data herein. The in vitro $IC_{50}$ concentrations have been from about 0.1 to about 3 micro molar. Such concentrations can be achieved in vivo by administering dosages of from about 100 to about 1,500 mg/day. It is known that at least in the lower half of this dosage range, d-tetrandrine is substantially nontoxic. It is believed that toxicity will be minimal even at the 1,500 mg/day range. The preferred method for administering the drug is orally, though other methods such as injection may be used.

It is not necessary that the d-tetrandrine or derivative be administered simultaneously with the principal drug. It is only important that they be administered sufficiently close together that the cancer is exposed to both simultaneously. For example, nude mice infected with a multidrug resistant human cancer were given 0.5 mg, 1 mg and 1.5 mg respectively in three separate injections, 72 hours apart. In different tests, they have then been injected with 5.5 mg per kg body weight doxorubicin either on the last day of the d-tetrandrine injections or two days thereafter. In both tests, the tumors were substantially reduced, if not altogether eliminated.

A woman with breast cancer was given d-tetrandrine orally, three times a day for a total of 180 mg per day, over a two week period. Five days after the beginning of that treatment, she was given a trichemo soup of 5-fluorouracil, cyclophosphamide and doxorubicin. Eight days later, near the end of the d-tetrandrine dosage, she was given 5-fluorouracil. This regime was followed two different times approximately two weeks apart during the course of retreatment. Her tumor was substantially eliminated.

For phase one clinical trails using d-tetrandrine, patients will receive ten different levels of d-tetrandrine, beginning at 100 mg/m$^2$, increasing by 100 mg/m$^2$ meter at each additional level until 1,000 mg/m$^2$ is reached. At a body area of 2 m$^2$, which is an 80 kg (about 200 pounds) person, this amounts to about 2000 mg/day. It is believed that the optimum human dosage will fall within the range of from about 50 mg/m$^2$ to about 800 mg/m$^2$. Each patient will receive this particular level for seven consecutive days. On day six, the patient will be given 60 mg/m$^2$ doxorubicin (adriamycin) intravenously. Converting from the conventionally used "m$^2$" measure to body weight (which of course varies and can only be approximated, which we did using 40 kg/m$^2$), it is believed that the optimum d-tetrandrine range will be from about 1 mg per kg to about 20 mg per kg. Sixty mg/m$^2$ doxorubicin (adriamycin) comprises about 1.5 mg per kg body weight.

The actual ratio of multidrug resistance reverser (i.e., the d-tetrandrine family member) and the primary anticancer drug will vary from cancer to cancer, patient to patient and from drug to drug. Typical recommended dosages for a number of primary cancer drugs are shown below:

| CLINICAL DOSES OF ANTICANCER DRUGS AFFECTED BY MDR MECHANISM | | | | |
|---|---|---|---|---|
| Drug | Dose mg/kg | Mg/m$^2$ | Route | How Often Given |
| Vinblastine | 0.1–0.4 | 1–2 | IV | once a week |
| Vincristine | 0.1–0.3 | 1–2 | IV | once a week |
| Etoposide (VP-16) | — | 50 mg / 100 mg | oral / oral | once a day/5 dys / alternate days-for a week |
| Teniposide (VM-26) | — | 50 mg | IV | each day/5 dys |
| Actinomycin D | 15 | — | IV | daily for 5 dys |
| Daunorubicin | 30–60 | — | IV | daily for 3 dys or once weekly |
| Doxorubicin (Adriamycin) | — | 60–70 | IV | once on day one second on day 21 |
| Mitoxantrone | — | 12 | IV | daily for 3 days |
| Taxol | 170–250 mg | — | subcutaneous | once every 3 wks |

The ratio of the reverser to the primary drug varies inversely. To a point, the use of a greater concentration of primary anticancer drug. This is desirable since the d-tetrandrine family members tend to be less toxic in vivo than do the known primary anticancer drugs. There may well be circumstances where one will want to exceed 800 mg/m$^2$/day reverser in order to facilitate use of less primary drug.

Thus, based on the data to date, it is believed that the optimum dosage procedure would be to administer the multidrug resistance reverser, i.e., d-tetrandrine or one of the other claimed family members, in oral doses of from about 50 to about 800 mg per square meter per day (probably in two or three doses per day) over a period of from about 4 to about 14 days. The primary anticancer drug would then be administered at usual dosages (possibly somewhat less in view of the potentiation effect of the resistance reverser) once or more during the course of the resistance reverser dosing. For example, during a four day period of d-tetrandrine administration, the primary anticancer drug would be administered on the beginning of the third day. Over a 14 day period, the primary anticancer drug or drugs might be administered on day 5 and day 10, or on days 4, 8 and 12.

In the treatment of various cancers whose cells are multidrug resistant, a member of the d-tetrandrine family as described above, or mixtures thereof, is administered in conjunction with primary drugs known to have effectiveness against particular cancers. The following are anti-cancer drugs which are pumped by the multidrug resistance mechanism: doxorubicin (adriamycin), vinblastine, vincristine, mythramycin (plicamycin), actinomycin D, colchicine, daunomycin, mitoxantrone, VP-16 (etoposide or podophyllotoxin), daunorubicin, taxol, VM26 (teniposide) and emetine.

The effectiveness of d-tetrandrine in reversing multidrug resistance and potentiating anticancer drugs in multidrug resistance cancer cells was determined with respect to three drug combinations: d-tetrandrine and doxorubicin; d-tetrandrine and vincristine; and d-tetrandrine and vinblastine. These combinations were investigated in the following multiple drug resistant human cancer cell lines: MES-SA/DX20 (the parent and doxorubicin-resistant cell lines from uterine leiomyosarcoma) and A2780/A2780AD10 (the parent and multiple drug resistant cell lines from an individual with ovarian cancer). The MES-SA/DX20 cell line was established according to the development methods of Sikic et al., *Resistance to Antineoplastic Drugs*, Chap. 3, CRC Press, Ed. David Kessel, pp. 37–47 (1989). In vitro drug sensitivity testing consisted of two assay models, the modified MTT assay (Mossman, J. Immunolog. Methods, Vol. 65, pp. 55–63, 1983) and the colonogenic assay. In addition to this, the combinations were investigated in vivo in nude mice bearing the DX20 cell line. The MTT assay was chosen because of its practical advantages in large-scale screening. The assay involved cellular conversion of tetrazolium salt to a colored formazan serving as a measurement of cell viability.

In a given experiment, culture media, 50 microliters, containing 8,000–25,000 cells, depending on the proliferation rate of the cell line, was pipetted into each well of several 96-well microtiter plates. The cells were allowed to attach overnight. 100 microliters of d-Tetrandrine-(S) solution, at a concentration below that established as an independent $IC_{50}$, was then added to each well of the plates. The cytotoxic drug, also at a concentration below that previously established as an $IC_{50}$, was then added at decreasing concentrations by 25% to several half plate sections. The cells were allowed to grown for 72 hours. 100 microliters of media was then removed and 25 microliters of 5 mg/ml MTT (Sigma, St. Louis, Mo.) in phosphate buffered saline was added to each well. The plates were kept in an incubator at 37° C. and 5% $CO_2$. After 2–3 hours of incubation, the extraction buffer containing 20% w/v SDS and 50% DMF was added and the plates again incubated overnight. The plates were read at a test wavelength of 570 nm on a multiwell spectrophotometer (Model MR 700, Dynatech Laboratories, Alexandria, Va.). Each drug combination was tested in triplicate. Percent survival was defined as percent of optical density (OD) of the drug-treated wells to that of the control detected by the spectrophotometer.

Figure 2:
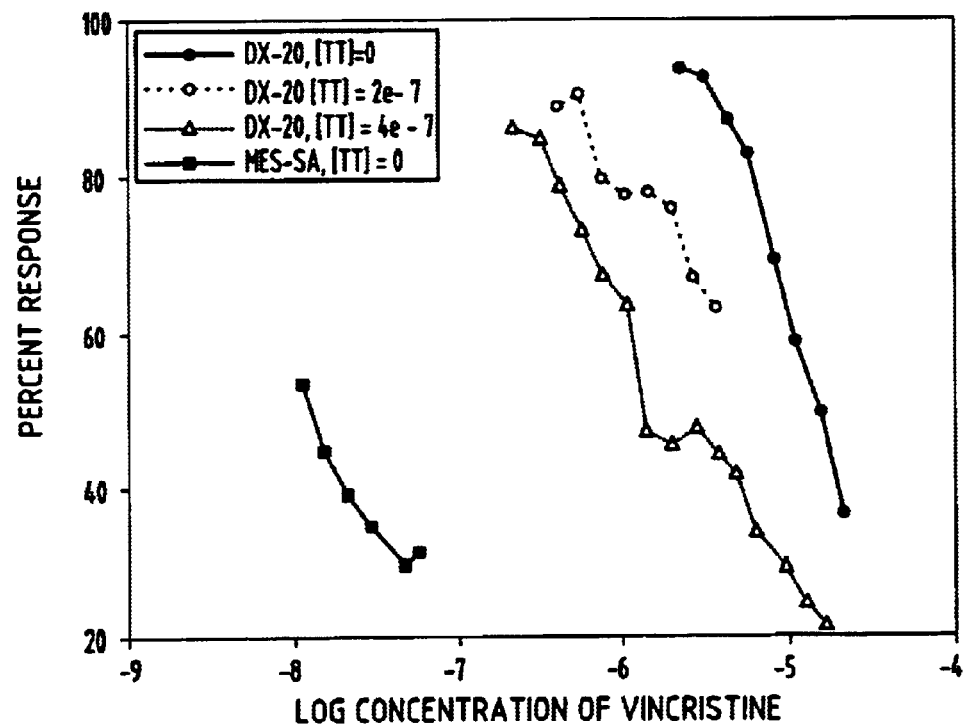
FIG. 2 is a graph comparing different concentrations of vincristine and d-tetrandrine alone and in combination when used against DX20 to parent MES-SA cells.
Figure 3:
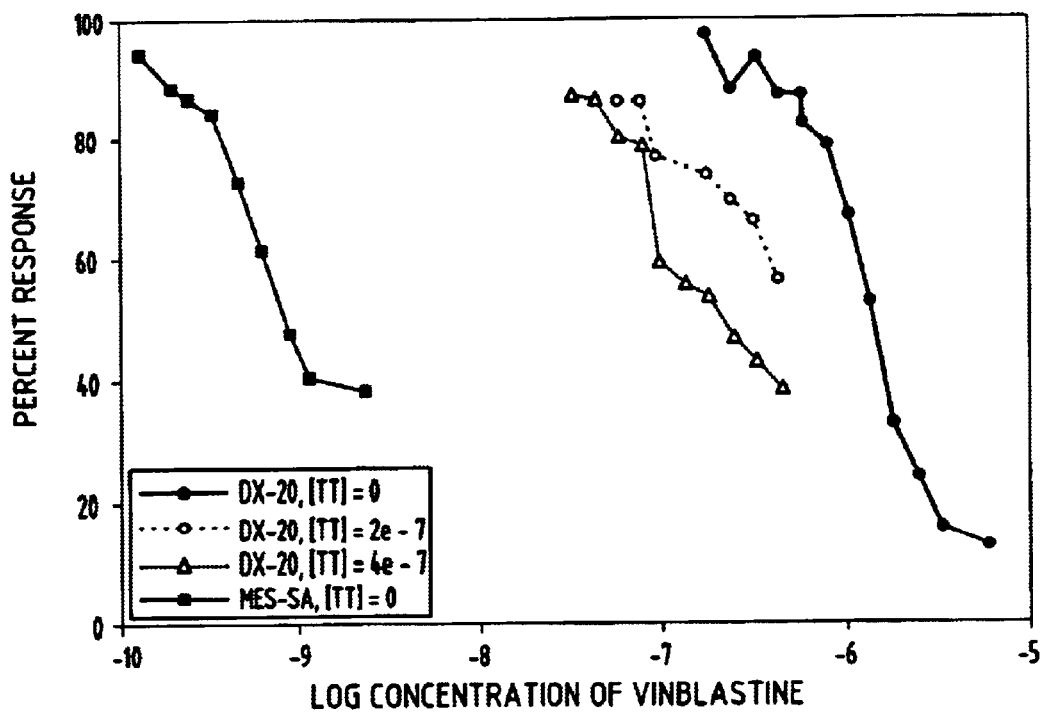
FIG. 3 is a graph comparing different concentrations of vinblastine and d-tetrandrine alone and in combination when used against DX20 to parent MES-SA cells.
Figure 4:
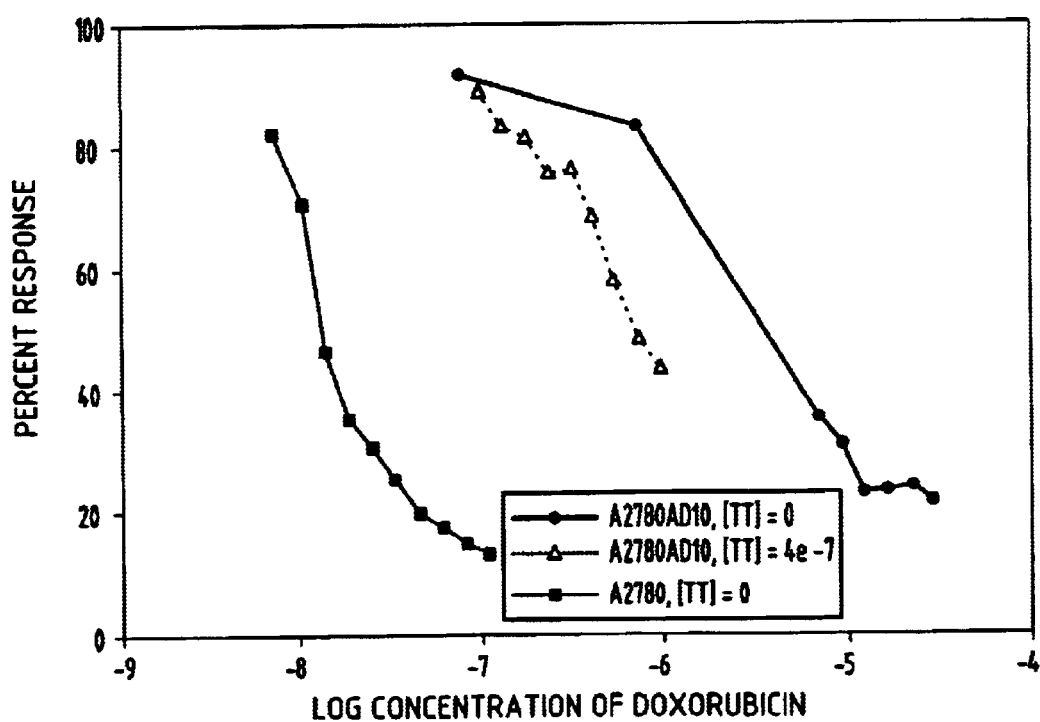
FIG. 4 is a graph comparing different concentrations of doxorubicin (adriamycin) and d-tetrandrine alone and in combination when used against A2780AD10 to parent A2780 cells.
Figure 5:
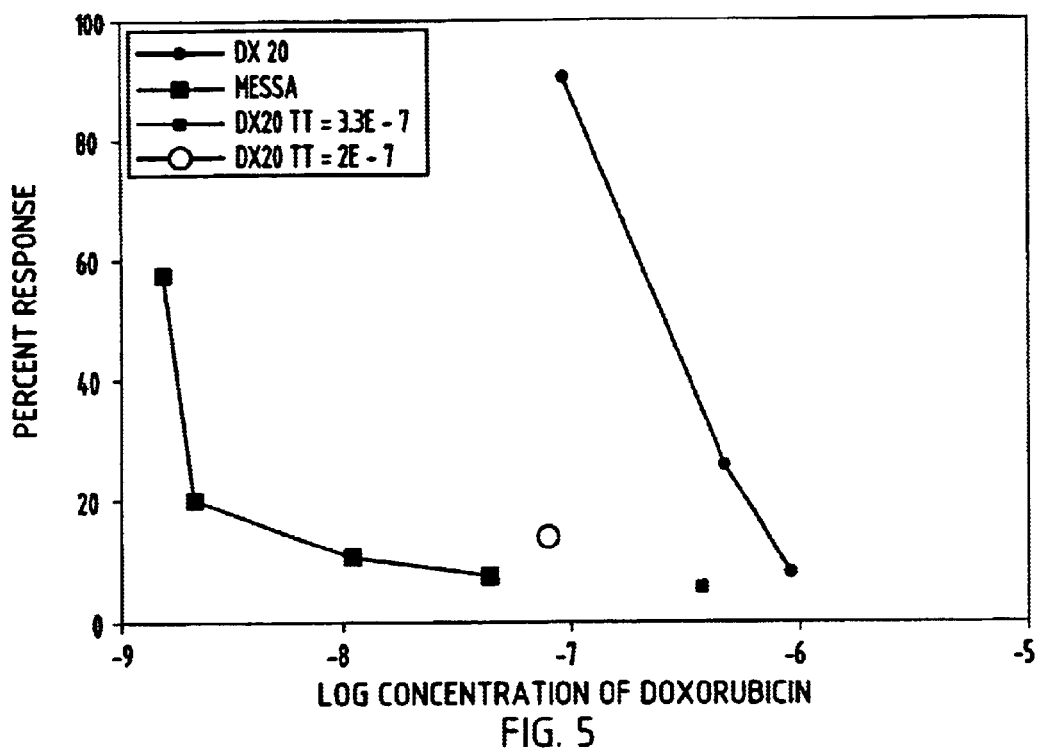
FIG. 5 is a graph comparing different concentrations of doxorubicin (adriamycin) and d-tetrandrine alone and in combination when used against DX20 to parent MES-SA cells.

FIGS. 1, 4 and 5 demonstrate that doxorubicin resistance can be either partially or completely reversed with the addition of d-tetrandrine. FIG. 1 demonstrates that when d-tetrandrine at $1.0 \times 10^{-6}$ M is combined with doxorubicin (adriamycin) at $1.2 \times 10^{-8}$ M there is a dramatic shift to the left. This shift demonstrates that the DX20 doxorubicin resistant cell line becomes more sensitive to doxorubicin than the parent (MES) cell line. The calculated $IC_{50}$ values also demonstrate that if the d-tetrandrine dose is increased from $2 \times 10^{-7}$ to $1 \times 10^{-6}$ the doxorubicin dose can be decreased from $6.6 \times 10^{-7}$ to $3.4 \times 10^{-8}$. FIGS. 2 and 3 demonstrate that vincristine-resistance and vinblastine resistance can be either partially or completely reversed with the addition of d-tetrandrine as well.

The second assay model used, colony formation assay, consisted of 1000–1500 cells, again depending on the proliferation rate of the cell line being added to each well of 24 well microtiter plates in 500 microliters of culture media. The cells were allowed to attach overnight. As in the MTT, culture media containing d-Tetrandrine-(S) and also a cytotoxic drug were added at concentrations below those previously established as independent $IC_{50}$ values. The plates were incubated for a total of 7 days before being fixed in 2.5% glutaraldehyde and stained with crystal violet. Quantitations of colony growth were assessed using an ultrasensitive imaging device (LCVS-5, I.P.S., Pittsburgh, Pa.). A colony is defined as any cluster of 30 or more cells. Percent inhibition was directly measured against control plates containing no drugs. FIG. 5 suggests also that doxorubicin-resistance can be either partially or completely reversed with the addition of d-tetrandrine.

Figure 9:
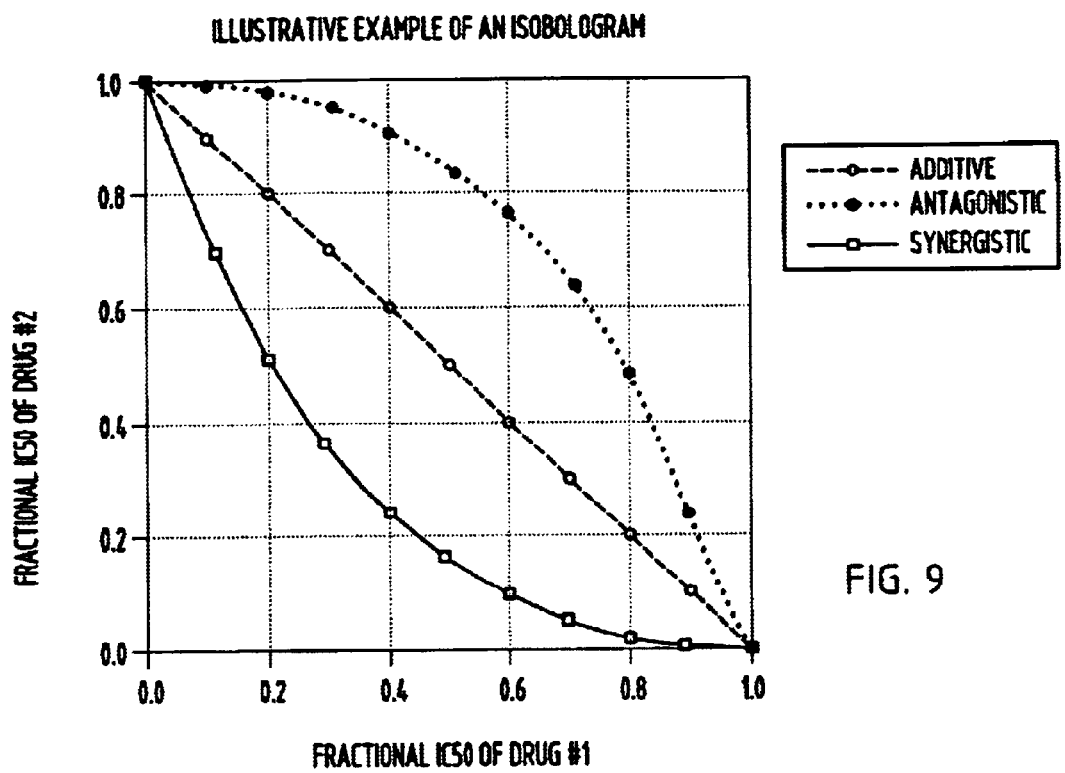
FIG. 9 is an illustrative example of an isobologram showing additive, antagonistic and synergistic effects.
Figure 10:
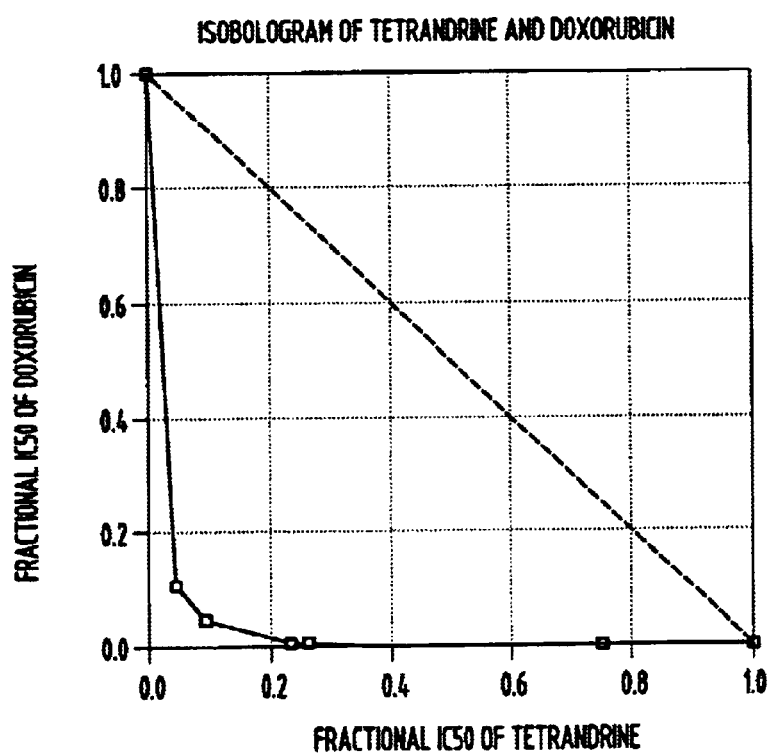
FIG. 10 is an actual isobologram of d-tetrandrine and doxorubicin.

Shown in FIG. 9 is an illustrative isobologram and shown in FIG. 10 is an actual isobologram of d-tetrandrine and doxorubicin. An isobologram allows one to quickly access the interaction of two compounds on a measured effect, in this case, killing a 75 fold multiple drug resistant tumor in vitro. The isobologram shows three possible cases: a straight line indicating additive effect, the bowed line above being typical of antagonism, and the lower line indicating synergism. The actual isobologram of d-tetrandrine and doxorubicin shows the tremendous synergism between doxorubicin and d-tetrandrine.

Figure 6:
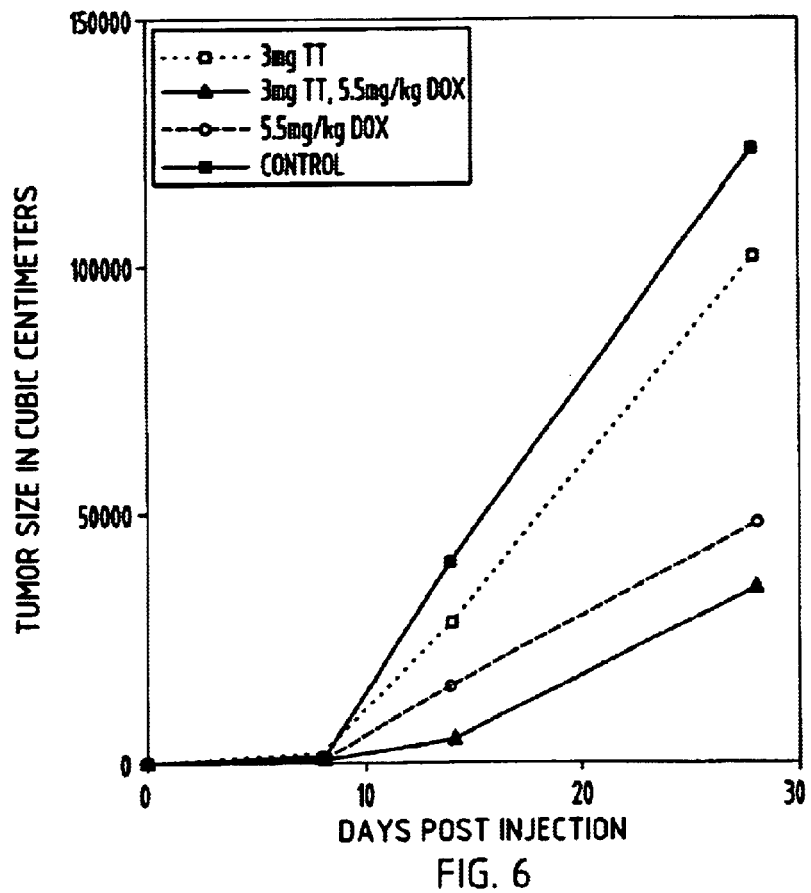
FIG. 6 is a graph demonstrating the effect doxorubicin (adriamycin) and d-tetrandrine used as a single agent have on tumor size.

In addition, the effects of d-Tetrandrine-(S) plus doxorubicin in Nu/Nu athymic mice inoculated with DX20 sarcoma cells, 76xresistant when compared to the parent MES-SA cells were examined. Four cohorts of nude animals bearing the DX20 tumor were treated in groups of 5 (control, doxorubicin, d-tetrandrine, and doxorubicin+d-tetrandrine). Initial data was gathered by monitoring tumor growth, comparing visible retardation in experimental groups receiving 2 cycles of d-Tetrandrine-(S) and doxorubicin over those receiving either d-Tetrandrine-(S) or doxorubicin alone in comparable amounts. (See FIG. 6). Tumor size was calculated using the formula (4 Pi/3) X*Y*2Z. Additional analysis showed that when given in 3 intraperitoneal injections over 120 hours, 150 mg/kg total, 54 micrograms/gram tissue d-Tetrandrine-(S) could be detected at the tumor. An $L.D._{50}$ dose of 260 mg/kg was also calculated by administering single escalating injections of the compound. Tables I & II and FIG. 6 give the actual measurements.

TABLE I

| | Tumor Measurements on Day 7 Prior to Treatment | | |
| --- | --- | --- | --- |
| | Length | Width | Depth |
| Control | 3.66 | 3.33 | 1.5 |
| Doxorubicin (adriamycin) | 3.50 | 3.87 | 1.25 |
| D-tetrandrine | 4.13 | 3.75 | 1.13 |
| Doxorubicin (adriamycin) + D-tetrandrine | 3.75 | 4.37 | 1.62 |

TABLE II

| | Tumor Measurements on Day 24 After Treatment | | |
| --- | --- | --- | --- |
| | Length | Width | Depth |
| Control | 30.50 | 25.00 | 21.50 |
| Doxorubicin (adriamycin) | 24.50 | 19.10 | 21.50 |
| D-tetrandrine | 30.60 | 26.16 | 24.66 |
| Doxorubicin (adriamycin) + D-tetrandrine | 18.00 | 13.62 | 12.75 |

The study was done with 3–4 week old male balb-C nude mice. The animals were injected with DX20 $1 \times 10^7$ cells. The animals were treated with d-tetrandrine on days 6, 8, 10 (1.5 mg, 1 mg, and 0.5 mg). the mice were given doxorubicin (adriamycin) 5.5 mg/kg on day 12.

In another test on nude mice, nude mice were inoculated with $1 \times 10^6$ cells of a multidrug resistant human cancer (DX20) and treatment was not initiated until the cancer had an opportunity to grow for 10 days. Some of the mice were treated only with d-tetrandrine at injections of 0.5 mg, 1 mg and 1.5 mg on days 10, 13 and 16 following first appearance of tumor. Another group were injected only with 5.5 mg per kg body weight doxorubicin at 14 days. Both groups of mice developed very large tumors which were unabated by either of these treatments. In fact, the tumors in the treated mice were approximately the same size as tumors in control mice who received no treatment at all.

In striking contrast, another group of mice were treated with a combination of doxorubicin and d-tetrandrine, each administered in the same manner as outlined above. In each of these mice, the tumor was substantially reduced by the end of the trial, approximately one month after treatment.

A woman with very serious breast cancer has also been successfully treated in accordance with the method of the present invention. The tables below describe her treatment regime, which involved a trichemo soup of 5-fluorouracil, cyclophosphamide and doxorubicin, administered intermittently with 5-fluorouracil alone. No d-tetrandrine was administered until day 95.

| Dates | Days | Treatment type* |
|---|---|---|
| 6/24 and 7/02 | 0 & 8 | Trichemo |
| 7/16 and 7/24 | 22 & 30 | Trichemo |
| 8/06 and 8/14 | 43 & 51 | Trichemo |
| 9/04 and 9/12 | 72 & 80 | Trichemo |
| 9/27 thru 10/11 | 95–109 | Tetrandrine |
| 10/02 and 10/08 | 100 & 108 | Trichemo |
| 10/26 thru 11/09 | 124–138 | Tetrandrine |
| 10/30 and 11/07 | 128 & 136 | Trichemo |
| 11/25 thru 12/12 | 154 to 171 | Tetrandrine |

*The two different treatments used

| Treatment Label | Treatment Description |
|---|---|
| "Trichemo" | On the first date, the following were administered:<br>5-fluorouracil: 850 mg (500 mg/m$^2$) I.V.<br>cyclophosphamide: 85 mg (50 mg/m$^2$) I.V.<br>adriamycin: 850 mg (500 mg/m$^2$) I.V.<br>On the second date (8 days later), the following was given:<br>5-fluorouracil: 850 mg (500 mg/m$^2$) I.V. |
| "Tetrandrine" | On every date in the range listed, the following was given:<br>tetrandrine: 60 mg t.i.d. p.o. (180 mg/day) |

Figure 11:
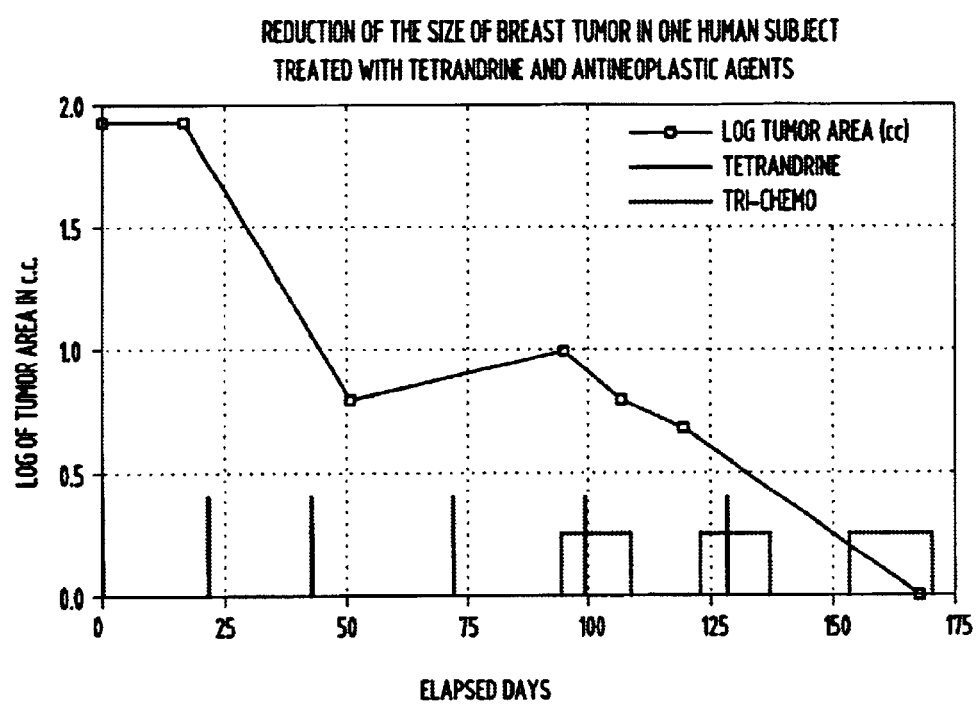
FIG. 11 is a graphical log of tumor area of a patient with very serious breast cancer.

FIG. 11 is a graphical log of her tumor area in cubic centimeters charted against days elapsed. The tumor initially responded to the trichemo treatment alone, reducing in size until day 50. After day 50, however, the tumor again began increasing in size until at day 95, d-tetrandrine was first administered. From that point, the tumor size continued to diminish to nonexistence by day 175.

The patient was diagnosed via biopsy on Mar. 19, 1991 as having an infiltrated carcinoma (poorly differentiated) on the right breast. She had had a history of non-malignant fibroid tumors to this time. She was treated with a combination of 5-fluorouracil, cyclophosphamide and doxorubicin according to the schedule shown below. She was also treated with tetrandrine as indicated (see table 2). Notice the increase in tumor size between days 50 and 100 indicating the formation of drug resistance.

Doxorubicin fluorescence tests were also conducted to confirm that multidrug resistant cells treated with d-tetrandrine actually absorb a greater concentration of doxorubicin than cells which were sensitive to doxorubicin alone. The fluorescence data shown in FIG. 12 demonstrate that even though the resistant cancel cells shows a lower concentration of doxorubicin than does a sensitive cancer, when doxorubicin is used alone, the doxorubicin concentration is actually greater in the resistant cancer than it is in the sensitive cancer when doxorubicin is used in conjunction with d-tetrandrine.

Figure 12:
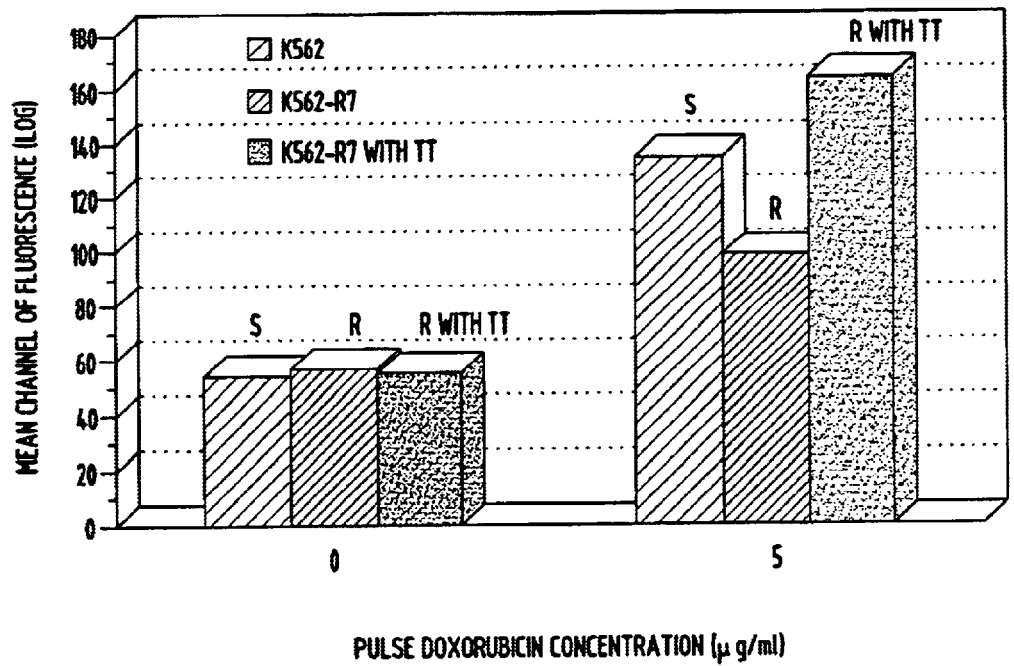
FIG. 12 is a bar graph showing the results of fluorescence data in sensitive (K652) and resistant (K562-R7) cancel cells untreated or pre-incubated with tetrandrine as measured by flow cytometry.

The data in FIG. 12 shows that tetrandrine keeps doxorubicin inside of MDR cancer cells. Notice that the sensitive strain exposed to doxorubicin produces more fluorescence than that of the resistant strain and thus contains more doxorubicin. The resistant strain pretreated with tetrandrine (TT) contains more doxorubicin than the sensitive strain.

Both in vitro and in vivo tests have been conducted using ethyl fangchinoline as the multidrug resistance reverser.

Referring to the structural formula above, $R_2$ for ethyl fangchinoline is $C_2H_5$.

The in vitro drug sensitivity testing of ethyl fangchinoline consisted of two assay models, the modified MTT (Mossman 1983) and a colony formation assay in which a direct measure was taken by quantitation of colony formation. The MTT assay was chosen because of its practical advantages in large scale screening. The assay involves cellular conversion of tetrozolium salt to a colored formazan serving as a measurement of cell viability.

Two human cell lines were chosen as the primary targets of study in reversing multiple-drug resistance. The MES-SA, a sarcoma, and its resistant subline, DX-20, were kindly donated by Dr. B. Sikic (U of Stanford, Stanford, Calif.). The A2780, an ovarian cancer, and its resistant subline, A2780-ad10, were provided by Roswell Park Memorial Inst. (Buffalo, N.Y.). All cell cultures were maintained in McCoys 5A and R.P.M.I., in the ovarian lines, culture media containing 10% F.B.S. Cells were subcultured routinely with tryp./EDTA, and drug resistance in the sublines was sustained by pulsing the cells with 1 ug/ml doxorubicin (adriamycin) for 96 hours every five to six weeks. All cell lines proved useful in the studies because of their rapid growth rate and the sensitivity of the parent lines to various chemo agents.

Culture media, 50 ul containing 8,000 to 25,000 cells depending on the proliferation rate of the line, was pipetted into each of 96 wells in a flat bottom tissue plate. The cells were incubated overnight to allow adherence. One hundred ul of ethyl fangchinoline, at a concentration below that previously established as an independent $IC_{50}$, was added to each experimental well. Doxorubicin, also at a concentration below that previously established as an independent $IC_{50}$, was added in varied concentrations to each experimental well. The plates were then incubated for 72 hours before MTT was added and the analysis of O.D. values interpreted by a multi-plate scanner (MR700, Dynatech).

The table below shows the $IC_{50}$ (or $ED_{50}$) molar concentrations for doxorubicin against the DX20 cancer cells in the presence of the indicated molar concentrations of ethyl fangchinoline on the one hand and d-tetrandrine on the other hand. Also indicated are the $IC_{50}$ molar concentrations against DX20 for doxorubicin alone, ethyl fangchinoline alone and d-tetrandrine alone.

| $IC_{50}$ TABLE FOR DOXORUBICIN AGAINST DX20 CANCER CELLS | | | |
|---|---|---|---|
| Molar Conc. of ethyl fang-chinoline or d-tetrandrine | $IC_{50}$ doxorubicin in ethyl fangchinoline | $IC_{50}$ doxorubicin in d-tetrandrine | $IC_{50}$ doxorubicin alone |
| $2 \times 10^{-7}$ | $4.7 \times 10^{-7}$ | $6.6 \times 10^{-7}$ | |
| $4 \times 10^{-7}$ | $1.6 \times 10^{-7}$ | $3.6 \times 10^{-7}$ | |
| $1 \times 10^{-6}$ | $4.8 \times 10^{-7}$ | $3.4 \times 10^{-7}$ | |
| 0 | | | $5.4 \times 10^{-6}$ |

$IC_{50}$ for ethyl fangchinoline alone: $6.5 \times 10^{-6}$
$IC_{50}$ for d-tetrandrine alone: $4.3 \times 10^{-6}$ In addition to in vitro studies, in vivo responses to ethyl fangchinoline were determined using NU/NU, a thymic mice carrying the DX20 tumor. As with d-tetrandrine and doxorubicin, these studies shown a definite response to treatment with ethyl fangchinoline and dox in the form of retarded growth of the rapid growing tumors, far below those treated with either ethyl fangchinoline or doxorubicin alone, as well as the controls, which received no treatments.

Additional studies show that ethyl fangchinoline, when administered i.p. over long periods of time with one low dose administration of dox, yields excellent results.

Figure 13:
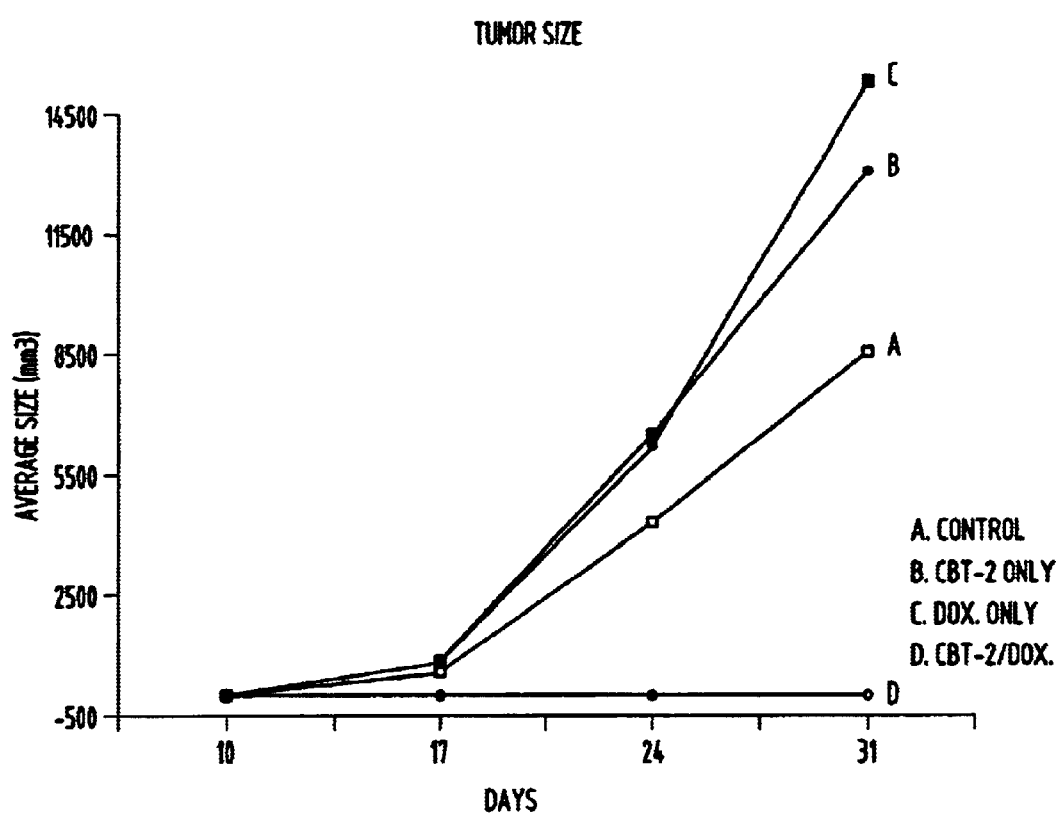
FIG. 13 is a graph of average tumor size in mice, which compares the effects of administering to mice d-tetrandrine alone, doxorubicin alone, and a combination of d-tetrandrine and doxorubicin in accordance with the invention.

In these studies, the nude mice were injected with $1 \times 10^6$ DX20 cancer cells. The mice in the control group received no treatment whatsoever. The mice in Group B received daily injections of 0.25 mg (approximately 13 mg per kg body weight) ethyl fangchinoline for 14 days after a tumor first appeared. Group C received one injection of 6 mg per kg body weight doxorubicin on day eight. The mice in Group D received the same ethyl fangchinoline injections for 14 days following the appearance of tumor as did the Group B mice. In addition, they received the same injection of doxorubicin on day eight as did the Group C mice. Average tumor size in cubic millimeters was measured on the mice in each group on day 10, 17, 24 and 31 (following initial appearance of the tumor). The striking results are shown in FIG. 13.

Survival rate studies indicate that the combination of doxorubicin and either ethyl fangchinoline or d-tetrandrine is no more toxic than doxorubicin alone.

The effectiveness of d-tetrandrine in potentiating antimalarial drugs in multidrug resistant parasitic malarial cells was determined by comparing the antimalarial action of d-tetrandrine and chloroquine alone and in combination against a *P. falciparum* malarial strain which is sensitive to chloroquine and another which is resistant to chloroquine. A similar study was conducted using d-tetrandrine and qinghaosu. Chloroquine and qinghaosu are commonly used antimalarial drugs.

Chemotherapy," Vol. 16, pages 710–718 (1979). Briefly, the final volume added to each of the ninety-six well microtitration plates was 250 microliters and consisted of 25 microliters of complete medium with or without the primary drug (chloroquine or qinghaosu), 175 microliters of either the parasitized culture or a nonparasitized human erythrocyte control, and 25 microliters of complete medium with or without d-tetrandrine. 25 microliters radioactive (0.5 microCi) [2,8-$^3$H] adenosine. The microtitration plates were incubated in a candle jar for an additional 18 hours, at 37° C.

As the malaria parasite grows $^3$H-adenosine is metabolized and incorporates into polymeric RNA and DNA. The labeled polymers are trapped on glass fiber filters and unincorporated material is washed away. In the absence of drug there is 100% incorporation of the labeled material. When drugs interfere (directly or indirectly), an inhibitory dose of 50% ($IC_{50}$) can be calculated. The experiments were repeated three times except where noted. Statistical analysis was done using Student's T-test for significance. Van Kyke et al. "Exp. Parasitol," Vol. 64, pages 418–423 (1987).

Figure 7:
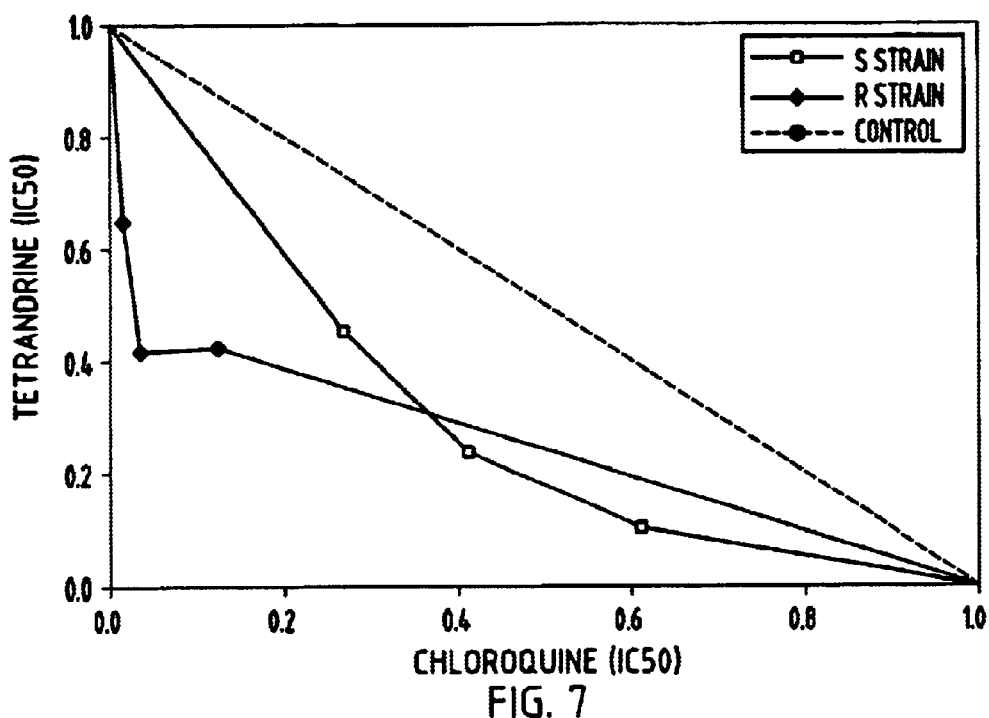
FIG. 7 is an isobologram showing the effectiveness of d-tetrandrine and chloroquine at 50% inhibition concentrations against sensitive and resistant malarial strains.
Figure 8:
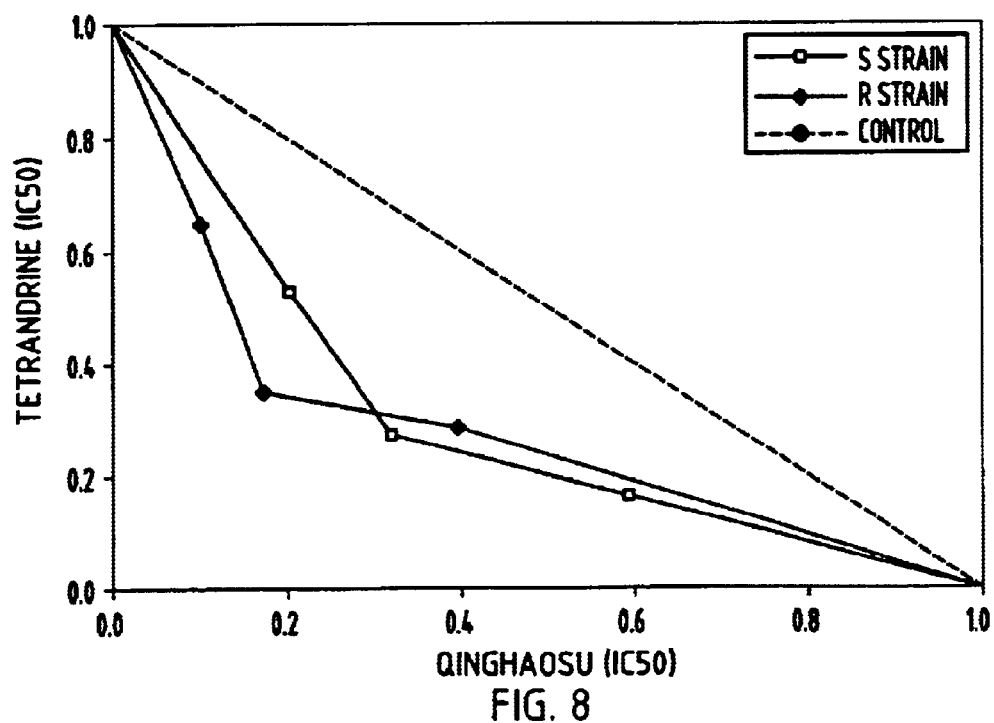
FIG. 8 is an isobologram showing the effectiveness of d-tetrandrine and qinghaosu at 50% inhibition concentrations against sensitive and resistant malarial strain.

When d-tetrandrine is added to chloroquine, it supplements and potentiates the antimalarial activity. When d-tetrandrine is added to qinghaosu or chloroquine, it provides long-acting and synergistic activity to qinghaosu or chloroquine. This can be seen in Tables III–VI and in FIGS. 7 & 8. Remarkably, when 3.0 micromolar d-tetrandrine is added to 0.1 micromolar chloroquine, the $IC_{50}$ of chloroquine can be lowered 43-Fold.

TABLE III $IC_{50}$ (nM) OF TT AND CQ FOR EACH DRUG ALONE AND IN COMBINATION*

| MALARIA* | SINGLE DRUG | | DRUG COMBINATION | | |
|---|---|---|---|---|---|
| | TT | CQ | TT(1.0 uM) CQ(0.3 uM) | TT(2.0 uM) CQ(0.2 uM) | TT(3.0 uM) CQ(0.1 uM) |
| S STRAIN | 498.1 ± 93.7 | 26.7 ± 3.8 | 54.9 ± 7.1(TT) 16.5 ± 2.1(CQ) | 114.1 ± 23.0(TT) 11.4 ± 2.3(CQ) | 223.3 ± 38.6(TT) 7.4 ± 1.3(CQ) |
| R STRAIN | 197.5 ± 24.7 | 185.8 ± 4.9 | 79.5 ± 13.7(TT) 23.8 ± 4.1(CQ) | 79.5 ± 16.1(TT) 8.0 ± 1.6(CQ) | 124.6 ± 9.6(TT) 4.2 ± 0.3(CQ) |

*The data in the table above are the mean values ± S.D (nM) from three experiments except where noted.
**Ratios of TT/CQ in the drug combinations are 10:3, 10:1 and 30:1 respectively.
***S and R strains represent CQ-sensitive (FCMSU1/Sudan) and resistant (w2) strain of *P. falciparum* respectively The dose ($IC_{50}$) of each drug or each drug combination required to effect a 50% inhibition in the malarial activity of each strain was determined by establishing a dose response curve for each.

FCMSU1/Sudan strain and cloned Indochina (W-2) strain of *P. falciparum* were used. The former is sensitive to chloroquine and the latter is resistant to chloroquine. The two strains of the parasite were cultured according to the candle jar method of Trager and Jensen, *Science*, Vol. 193, pages 673–675 (1976). In a given experiment, four-day-old Petri dish cultures (approximately 10% parasitemia) were diluted with medium containing an amount of noninfected type A human erythrocytes to obtain a culture with a final hematocrit of 1.5% and parasitemia of 0.5–1.0%. The resulting culture was ready for addition to microtitration plates with ninety-six flat-bottom wells.

The testing procedure used was similar to that described by Desjardins et al. in "Antimicrobial Agents and When the inhibiting activity of two drugs, e.g., A and B are compared, the middle point of the dose response curve is usually chosen as the basis for comparison. This point is known as the inhibitory dose that occurs at the point of 50% inhibition of the response to be measured (inhibitory concentration at 50% inhibitory response=$IC_{50}$). An isobologram is developed by comparing the $IC_{50}$ of one drug against the other, i.e., drug A against drug B. We start by putting the $IC_{50}$ of drug B at the top of the y axis marked 1.0. The $IC_{50}$ of drug A is placed at the position 1.0 on the x axis. The combinations of drug A and drug B are mixed and tested that are below $IC_{50}$ of either drug and the points are located on the graph. If the two drugs are additive, there is a straight line between the $Y_1 Y_0$ (drug B) and $Y_0 Y_1$ (drug A). If the line or curve bends below the straight line, the drugs are synergistic or potentiating. If the line bends above the straight line, the two drugs are antagonistic (see FIG. 9).

TABLE IV

$IC_{50}$ (nM) OF TT AND QHS FOR EACH DRUG ALONE AND IN COMBINATION*

| | SINGLE DRUG | | DRUG COMBINATION** | | |
|---|---|---|---|---|---|
| | | | TT(1.0 uM) | TT(2.0 uM) | TT(3.0 uM) |
| MALARIA** | TT | QHS | QHS(0.3 uM) | QHS(0.2 uM) | QHS(0.1 uM) |
| S STRAIN | 410.2 ± 69.0 | 36.7 ± 4.7 | 71.9 ± 8.9(TT) | 113.5 ± 6.3(TT) | 219.5 ± 35.5(TT) |
| | | | 21.6 ± 2.7(QHS) | 11.4 ± 0.6(QHS) | 7.3 ± 1.2(QHS) |
| R STRAIN | 205.6 ± 49.8 | 47.8 ± 14.5 | 59.6 ± 13.7(TT) | 71.8 ± 13.8(TT) | 136.9 ± 41.6(TT) |
| | | | 17.9 ± 4.1(QHS) | 7.2 ± 1.4(QHS) | 4.6 ± 1.4(QHS) |

*The data in the table above are the mean values ± S.D (nM) from three experiments except where noted.
**Ratios of TT/QHS in the drug combinations are 10:3, 10:1 and 30:1 respectively.
***S and R strains represent CQ-sensitive (FCMSU1/Sudan) and resistant (W2) strain of *P. falciparum* respectively.

TABLE V

EFFECT OF COMBINATION OF TETRANDRINE AND CHLOROQUINE ON *P. FALCIPARUM*

| | | SFIC* | | |
|---|---|---|---|---|
| | | 1.0 uM TT | 2.0 uM TT | 3.0 uM TT |
| MALARIA** | TRIAL | 0.3 uM CQ | 0.2 uM CQ | 0.1 uM CQ |
| S STRAIN | 1 | 0.77 | 0.66 | 0.73 |
| | 2 | 0.64 | 0.77 | 0.70 |
| | 3 | 0.78 | 0.55 | 0.75 |
| | MEAN ± S.D | 0.73 ± 0.06 | 0.66 ± 0.09 | 0.73 ± 0.02 |
| R STRAIN | 1 | 0.60 | 0.45 | 0.74 |
| | 2 | 0.68 | 0.63 | 0.76 |
| | 3 | 0.36 | 0.30 | 0.50 |
| | MEAN ± S.D | 0.55 ± 0.14 | 0.46 ± 0.14 | 0.67 ± 0.12 |

*SFIC represents sum of fractional inhibitory concentration as described by Berenbaum (11), SFIC is equal to one in cases of additive effects of the drugs, higher than one in cases of antagonism and lower than one in synergistic action.
**S and R strain: chloroquine sensitive (FCMSU1/Sudan) and resistant (w2) strain of *P. falciparum*.

TABLE VI

EFFECT OF COMBINATION OF TETRANDRINE AND QINGHAOSU ON *P. FALCIPARUM*

| | | SFIC* | | |
|---|---|---|---|---|
| | | 1.0 uM TT | 2.0 uM TT | 3.0 uM TT |
| MALARIA** | TRIAL | 0.3 uM QHS | 0.2 uM QHS | 0.1 uM QHS |
| S STRAIN | 1 | 0.77 | 0.68 | 0.71 |
| | 2 | 0.74 | 0.49 | 0.72 |
| | 3 | 0.79 | 0.62 | 0.77 |
| | MEAN ± S.D | 0.77 ± 0.02 | 0.60 ± 0.08 | 0.73 ± 0.03 |
| R STRAIN | 1 | 0.63 | 0.46 | 0.71 |
| | 2 | 0.77 | 0.72 | 0.74 |
| | 3 | 0.64 | 0.40 | 0.81 |
| | MEAN ± S.D | 0.68 ± 0.06 | 0.52 ± 0.14 | 0.75 ± 0.04 |

*SFIC represents sum of fractional inhibitory concentration as described by Berenbaum (11), SFIC is equal to one in cases of additive effects of the drugs, higher than one in cases of antagonism and lower than one in synergistic action.
**S and R strain: chloroquine sensitive (FCMSU1/Sudan) and resistant (W2) strains of *P. falciparum*.

In an attempt to explain this surprising result, d-tetrandrine and various of its derivatives and several nontetrandrine derivatives were tested for their individual effectiveness against a chloroquine sensitive and a chloroquine resistant strain of *P falciparum* malaria. The test procedure was basically the same as outlined above. The nonfamily members were cycleanine, cepharanthine, methoxadiantifoline and thalicarpine, whose structural formulas are illustrated herebelow:

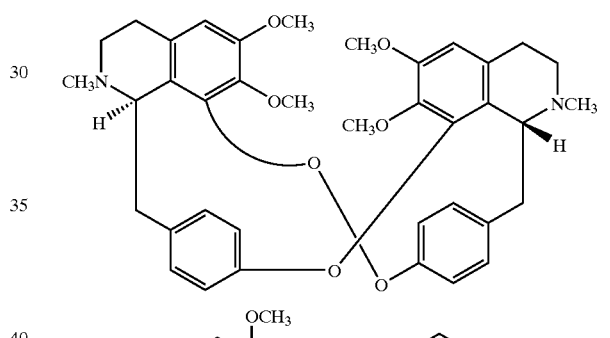

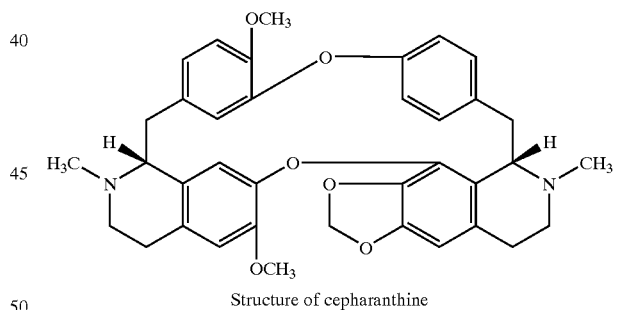

Structure of cepharanthine

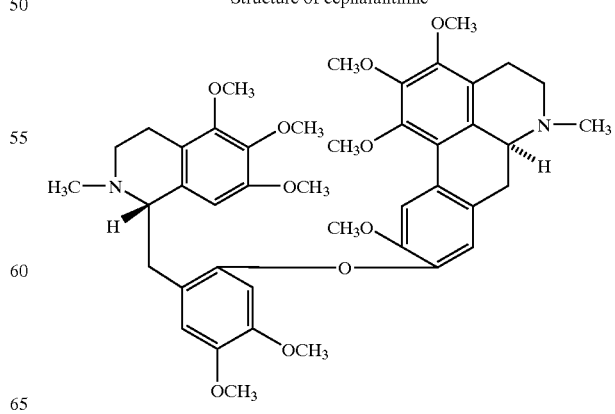

METHOX ADIANTIFOLINE

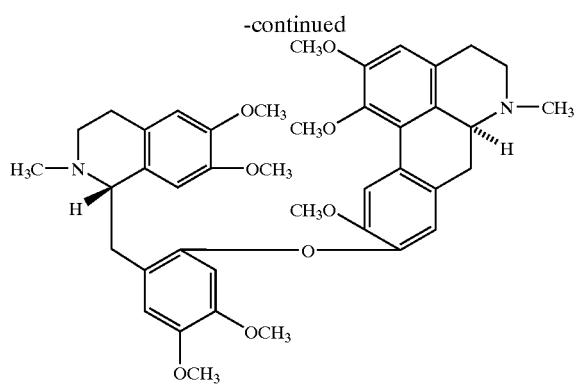

THALICARPINE

These Comparative Activities are set forth in Table VII Below

The foregoing illustrates that the drugs of the present invention provide a treatment for multidrug resistance, whether occurring naturally within a cell or whether occurring through infection in a cell. The present invention is directed primarily to a method for treating such multidrug resistance infection. The drugs of the present invention potentiate the action of primary drugs known to be effective against the multidrug resistance infected disease cells.

Of course it is understood that the above is merely a preferred embodiment of the invention and that various changes and alterations can be made without departing from the spirit and the broader aspects thereof.

What is claimed is:

1. A method for treating and thereby reducing drug resistant uterine, ovarian, breast, lymphoma, cartilage/bone, leukemia, liver, abdominal area, lung, cervical, pelvic, adrenal gland, iliac, Hodgkin's disease and thyroid cancers in a patient comprising:

CHEMICAL STRUCTURE ANTIMALARIAL ACTIVITY OF BISBENZYL ISOQUINOLINE ALKALOIDS AGAINST *PLASMODIUM FALCIPARUM* IN VITRO

| Drug (a) | Configuration | | Substituents | | | | Oxygen Bridge | $IC_{50}$ ($10^{-7}$M) | | Ratio (S/R)* |
|---|---|---|---|---|---|---|---|---|---|---|
| | C-1 | C-1' | C-5 | C-7 | C-12 | C-5' | | S** | R** | |
| TT | S | S | H | OCH3 | OCH3 | | C8–C7' C11–C12' | 2.9 | 1.2 | 2.6 |
| IT | R | S | H | OCH3 | OCH3 | | C8–7' C11–C12' | 4.8 | 1.4 | 3.5 |
| HE | S | S | OCH3 | OCH3 | OCH3 | | C8–C7' C11–C12' | 3.7 | 1.3 | 2.8 |
| BB | R | S | H | OCH3 | OH | | C8–C7' C11–C12' | 4.6 | 1.9 | 2.7 |
| PY | R | R | H | OCH3 | OH | | C8–C7' C11–C12' | 3.8 | 4.2 | 0.9 |
| PH | R | R | H | OCH3 | OCH3 | | C8–C7' C11–C12' | 6.0 | 5.0 | 1.2 |
| OB | R | S | H | OH | OH | | C8–C7' C11–C12' | 6.6 | 4.8 | 1.5 |
| TA | S | S | H | OH | OCH3 | | C8–C7' C11–C12' | 2.6 | 2.2 | 1.2 |
| CY | R | R | H | OCH3 | | | C8–C12' C12–C8' | 32 | 42 | 0.8 |
| CE | S | R | H | OCH2 | | | C8–C7' C12–C11' | 10 | 9.4 | 1.1 |
| ME | S | S | OCH3 | OCH3 | OCH3 | OCH3 | C10–C12' | 53 | 9.7 | 5.5 |
| TH | S | S | H | OCH3 | OCH3 | H | C10–C12' | 17 | 13 | 1.3 |

(a): TT—tetrandrine; IT—isotetrandrine; HE—hernandezine; BB—berbamine; PY—pycnamine; PH—phacanthine; OB—obamegine; FA—fangchinoline; CY—cycleanine; CE—cepharanthine; ME—methoxadiantifoline; TH—thalicarpine
*$IC_{50}$ of a drug against sensitive strain of *P. falciparum* is devided by $IC_{50}$ for resistant strain.
**S and R represent chloroquine-sensitive and resistant strain of *P. falciparum*.

The results of Table VII illustrate that methoxadiantifoline and those members of the d-tetrandrine family having the "S" isomeric configuration at the C-1' chiral carbon and having at least one of the $R_2$ substituent comprising $CH_3$ are actually substantially more effective against the chloroquine resistant malarial strain than against the chloroquine sensitive malarial strain. This extremely surprising result suggests that these compounds actually reverse or inhibit the pumping action of the glycoprotein associated with such multidrug resistant cells. Instead of pumping the toxic drug out of the cell, it actually appears to be pumping a lesser concentration of the toxic drug out of the cell. At present, this is the only reasonable explanation for these surprising results, since the only known significant difference between the multidrug resistant cells and the corresponding drug sensitive cells is the substantially greater percentage of P-glycoprotein associated with the multidrug resistant cell.

administering to the patient in vivo effective concentration of (1) a compound having the following formula:

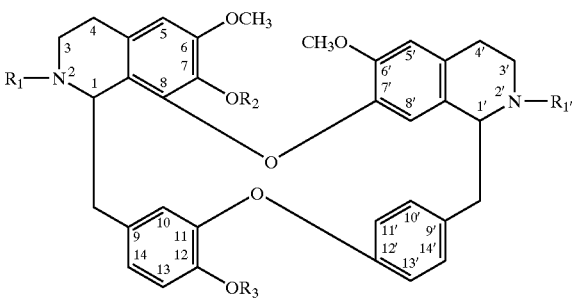

where $R_1$ and $R_1'$ are the same or different short chained carbon based moieties; $R_2$ is $CH_3$ or $C_2H_5$ and $R_3$ is $CH_3$ or Hydrogen, and the isomeric configuration at the C-1' chiral carbon location is "S", and (2) at least one principal drug known to be effective for treating whichever of said cancers is being treated, administered sufficiently contemporaneously with said compound that said cancer is exposed to said compound and said principal drug simultaneously.

2. The method of claim 1 in which said compound is used at a dosage level of from about 50 to about 1000 mg per square meter per day.

3. The method of claim 2 in which said principal drug is doxorubicin.

4. The method of claim 2 in which said principal drug is vinblastine.

5. The method of claim 1 in which said principal drug is vincristine.

6. The method of claim 1 in which said principal drug is taxol.

7. The method of claim 1 in which said principal drug is one of doxorubicin, vincristine, vinblastine, taxol, etoposide, 5-fluorouracil, cyclophosphamide and mixtures thereof.

8. The method of claim 7 in which $R_2$ in said compound (1) is $CH_3$ and $R_3$ is $CH_3$.

9. The method of claim 7 in which $R_2$ in said compound (1) is $C_2H_5$ and $R_3$ is $CH_3$.

10. The method of claim 7 in which said compound and said principal drug are administered in a cycle as follows: said compound is administered to said patient approximately daily over a period of from about 4 to about 14 days, and said principal drug is administered to said patient at least once during the period of time from day 4 to day 14.

11. The method of claim 10 in which said cycle is repeated approximately every 30 days until said cancer abates.

12. The method of claim 11 in which $R_2$ in said compound (1) is $CH_3$ and $R_3$ is $CH_3$.

13. The method of claim 11 in which $R_2$ in said compound (1) is $C_2H_5$ and $R_3$ is $CH_3$.

14. The method of claim 2 in which $R_2$ in said compound (1) is $CH_3$ and $R_3$ is $CH_3$.

15. The method of claim 2 in which $R_2$ in said compound (1) is $C_2H_5$ and $R_3$ is $CH_3$.

16. The method of claim 1 in which said compound and said principal drug are administered in a cycle as follows: said compound is administered to said patient approximately daily over a period of from about 4 to about 14 days, and said principal drug is administered to said patient at least once during the period of time from day 4 to day 14.

17. The method of claim 16 in which said cycle is repeated approximately every 30 days until said cancer abates.

18. The method of claim 17 in which said compound is administered at a rate of from about 50 to about 1000 mg per square meter per day.

19. A pharmaceutical composition for treating multidrug resistant disease other than tuberculosis comprising: a mixture of (1) a compound having the following formula

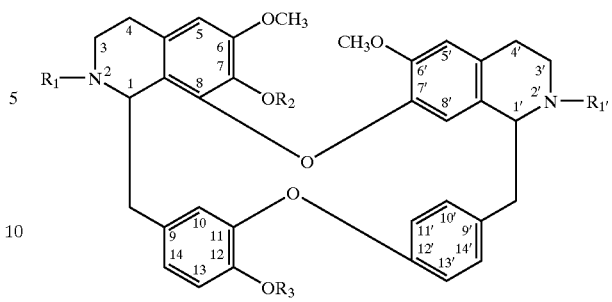

where $R_1$ and $R_1'$ are the same or different short chained carbon based moieties; $R_2$ is $CH_3$ or $C_2H_5$ and $R_3$ is $CH_3$ or Hydrogen, and the isomeric configuration at the C-1' chiral carbon location is "S", and (2) at least one principal drug known to be effective in treating non-multidrug resistant strains of said disease.

20. The pharmaceutical composition of claim 19 in which $R_2$ in said compound (1) is $CH_3$ and $R_3$ is $CH_3$.

21. The pharmaceutical composition of claim 19 in which $R_2$ in said compound (1) is $C_2H_5$ and $R_3$ is $CH_3$.

22. The pharmaceutical composition of claim 19 in which said principal drug comprises: one of the anticancer drugs doxorubicin, vincristine, vinblastine, mythramycin, actinomycin D, colchicine, daunomycin, mitoxantrone, etoposide, daunorubicin, taxol, VM-26, emetine, 5-fluorouracil, cyclophosphamide and mixtures thereof.

23. The pharmaceutical composition of claim 19 in which said principal drug comprises one of chloroquine, qinghaosu and mixtures thereof.

24. A pharmaceutical kit comprising (1) a multidrug resistance reverser compound having the following formula:

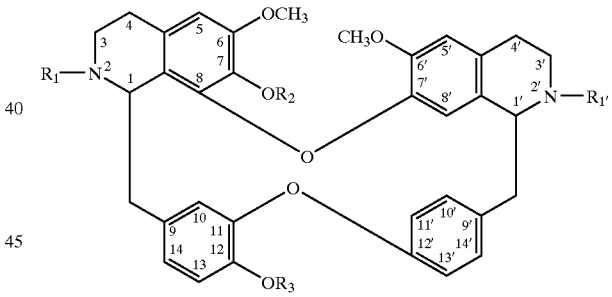

where $R_1$ and $R_1'$ are the same or different short chained carbon based moieties; $R_2$ is $CH_3$ or $C_2H_5$ and $R_3$ is $CH_3$ or Hydrogen, and the isomeric configuration at the C-1' chiral carbon location is "S", and (2) a principal drug known to be effective against a particular disease to be treated other than tuberculosis.

25. The pharmaceutical kit of claim 24 in which $R_2$ in said compound (1) is $CH_3$ and $R_3$ is $CH_3$.

26. The pharmaceutical kit of claim 24 in which $R_2$ in said compound (1) is $C_2H_5$ and $R_3$ is $CH_3$.

27. The pharmaceutical kit of claim 24 in which said principal drug comprises: one of the anticancer drugs doxorubicin, vincristine, vinblastine, mythramycin, actinomycin D, colchicine, daunomycin, mitoxantrone, etoposide, daunorubicin, taxol, VM-26, emetine, 5-fluorouracil, cyclophosphamide and mixtures thereof.

28. The pharmaceutical kit of claim 24 in which said principal drug comprises one of chloroquine, qinghaosu and mixtures thereof.

29. A method for treating a multidrug resistant disease comprising: exposing the multidrug resistant disease cells other than tuberculosis to effective concentrations of a compound having the following formula:

where $R_1$ and $R_1'$ are the same or different short chained carbon based moieties; $R_2$ is $CH_3$ or $C_2H_5$ and $R_3$ is $CH_3$ or Hydrogen, and the isomeric configuration at the C-1' chiral carbon location is "S".

30. The pharmaceutical composition of claim 19 in which the ratio of said compound to said principal drug is from about 0.04 to about 170.

31. The pharmaceutical composition of claim 30 in which said principal drug comprises: one of the anticancer drugs doxorubicin, vincristine, vinblastine, mythramycin, actinomycin D, colchicine, daunomycin, mitoxantrone, etoposide, daunorubicin, taxol, VM-26, emetine, 5-fluorouracil, cyclophosphamide and mixtures thereof.

32. The composition of claim 30 in which said principal drug is one of doxorubicin, vincristine, vinblastine, taxol, etoposide, 5-fluorouracil, cyclophosphamide and mixtures thereof.

33. The pharmaceutical composition of claim 32 in which $R_2$ in said compound (1) is $CH_3$ and $R_3$ is $CH_3$.

34. The pharmaceutical composition of claim 32 in which $R_2$ in said compound (1) is $C_2H_5$ and $R_3$ is $CH_3$.

35. The pharmaceutical kit of claim 24 in which said multidrug resistance reverser is present in quantities sufficient to administer from about 50 to about 1000 mg per square meter per day for from about 4 to about 14 days, and said principal drug is present in an amount known to be effective against the particular disease which it is used to treat.

36. The pharmaceutical kit of claim 31 in which said principal drug comprises: one of the anticancer drugs doxorubicin, vincristine, vinblastine, mythramycin, actinomycin D, colchicine, daunomycin, mitoxantrone, etoposide, daunorubicin, taxol, VM-26, emetine, 5-fluorouracil, cyclophosphamide and mixtures thereof.

37. The pharmaceutical kit of claim 31 in which said principal drug is one of doxorubicin, vincristine, vinblastine, taxol, etoposide, 5-fluorouracil, cyclophosphamide and mixtures thereof.

38. The pharmaceutical kit of claim 31 in which $R_2$ in said compound (1) is $CH_3$ and $R_3$ is $CH_3$.

39. The pharmaceutical kit of claim 31 in which $R_2$ in said compound (1) is $C_2H_5$ and $R_3$ is $CH_3$.

40. A method for treating and thereby reducing multidrug resistant cancer in a patient by potentiating a primary anti-cancer drug to which said cancer exhibits multidrug resistance comprising: administering to a patient in vivo, and thereby exposing the patient's multidrug resistant cancer cells to: (1) effective concentrations of a compound having the following formula:

where $R_1$ and $R_1'$ are the same or different short chained carbon based moieties; $R_2$ is $CH_3$ or $C_2H_5$ and $R_3$ is $CH_3$ or Hydrogen, and the isomeric configuration at the C-1' chiral carbon location is "S"; and (2) effective concentrations of a primary anti-cancer drug known to be effective against non-drug resistant strains of the cancer being treated; said administration being sufficiently contemporaneous to simultaneously expose said drug resistant cancer cells to both (1) and (2).

41. The method of claim 40 in which said compound is d-tetrandrine.

42. The method of claim 41 in which said compound is used at a dosage level of from about 50 to 1000 mg/m² per day.

43. The method of claim 42 in which the primary drug is one of doxorubicin, vincristine, vinblastine, taxol, etoposide, 5-fluorouracil, cyclophosphamide and mixtures thereof.

44. The method of claim 40 in which said compound is used at a dosage level of from about 50 to 1000 mg/m² per day.

45. The method of claim 40 wherein said primary drug is one of doxorubicin, vincristine, vinblastine, taxol, etoposide, 5-fluorouracil, cyclophosphamide and mixtures thereof.

46. The method of claim 44 in which said compound is ethyl fangchinoline and the principal drug is doxorubicin.

47. The method of claim 46 in which said compound is administered at between 50 and 1000 mg/m².

48. The method of claim 45 in which said compound is administered at between 50 and 800 mg/m².

49. The method of claim 45 in which said compound and said primary drug are administered in a cycle as follows: said compound is administered to said patient approximately daily over a period of from about 4 to about 14 days, and said primary drug is administered to said patient at least once during the period of time from day 4 to day 14.

50. The method of claim 49 in which said cycle is repeated approximately every 30 days until said cancer abates.

51. The method of claim 50 in which said compound is used at a dosage level of from about 50 to 1000 mg/m² per day.

52. The method of claim 51 in which $R_2$ in said compound (1) is $CH_3$ and $R_3$ is $CH_3$.

53. The method of claim 51 in which $R_2$ in said compound (1) is $C_2H_5$ and $R_3$ is $CH_3$.

54. The method of claim 40 in which said compound and said primary drug are administered in a cycle as follows: said compound is administered to said patient approximately daily over a period of from about 4 to about 14 days, and said primary drug is administered to said patient at least once during the period of time from day 4 to day 14.

55. The method of claim 54 in which said cycle is repeated approximately every 30 days until said cancer abates.

56. The method of claim 55 in which said compound is used at a dosage level of from about 50 to 1000 mg/m² per day.

57. The method of claim 56 in which $R_2$ in said compound (1) is $CH_3$ and $R_3$ is $CH_3$.

58. The method of claim 56 in which $R_2$ in said compound (1) is $C_2H_5$ and $R_3$ is $CH_3$.

59. The method of claim 45 in which $R_2$ in said compound (1) is $CH_3$ and $R_3$ is $CH_3$.

60. The method of claim 45 in which $R_2$ in said compound (1) is $C_2H_5$ and $R_3$ is $CH_3$.

61. The method of claim 45 in which said cancer is tumorous cancer.

62. The method of claim 40 in which said cancer is tumorous cancer.

63. A method for treating and thereby reducing drug resistant cancer in a patient comprising:

administering to the patient in vivo effective concentrations of (1) a compound having the following formula:

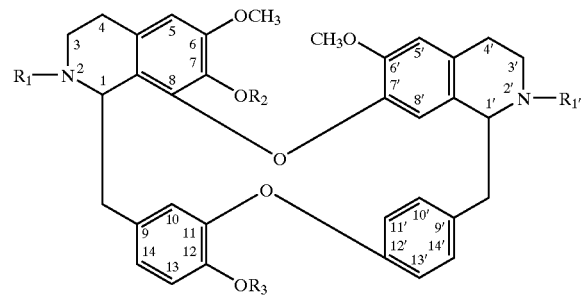

where $R_1$ and $R_1'$ are the same or different short chained carbon based moieties; $R_2$ is $CH_3$ or $C_2H_5$ and $R_3$ is $CH_3$ or Hydrogen, and the isomeric configuration at the C-1' chiral carbon location is "S"; and (2) one of the anti-cancer drugs adriamycin (doxorubicin), vincristine, vinblastine, mythramycin, actinomycin D, colchicine, daunomycin, mitoxantrone, etoposide, daunorubicin, taxol, VM-26, emetine, 5-fluorouracil, cyclophosphamide and mixtures thereof; said administration being sufficiently contemporaneous to simultaneously expose said drug resistant cancer cells to both (1) and (2).

64. The method of claim 63 in which $R_2$ in said compound (1) is $CH_3$ and $R_3$ is $CH_3$.

65. The method of claim 63 in which $R_2$ in said compound (1) is $C_2H_5$ and $R_3$ is $CH_3$.

66. The method of claim 63 in which said anticancer drug is doxorubicin.

67. The method of claim 66 in which $R_2$ in said compound (1) is $CH_3$ and $R_3$ is $CH_3$.

68. The method of claim 66 in which $R_2$ in said compound (1) is $C_2H_5$ and $R_3$ is $CH_3$.

69. The method of claim 63 in which the disease treated is tumorous cancer.

70. The method of claim 69 in which said compound is administered at between about 50 and 1000 mg/m².

71. The method of claim 70 in which $R_2$ in said compound (1) is $CH_3$ and $R_3$ is $CH_3$.

72. The method of claim 70 in which $R_2$ in said compound (1) is $C_2H_5$ and $R_3$ is $CH_3$.

73. A method for treating and thereby reducing drug resistant uterine, ovarian, breast, lymphoma, cartilage/bone, leukemia, liver, abdominal area, lung, cervical, pelvic, adrenal gland, iliac, Hodgkin's disease and thyroid cancers in a patient comprising:

administering to the patient in vivo an effective concentration of (1) a compound having the formula:

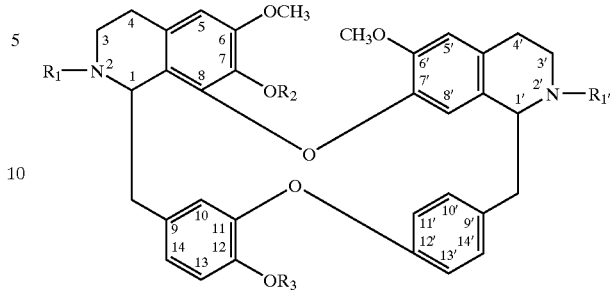

where $R_1$ and $R_1'$ are the same or different short chained carbon based moieties; $R_2$ is $CH_3$ or $C_2H_5$ and $R_3$ is $CH_3$ or Hydrogen, and the isomeric configuration at the C-1' chiral carbon location is "S", and (2) at least one principal drug known to be effective for treating whichever of said cancers is being treated, said principal drug being one of doxorubicin, vincristine, vinblastine, taxol, etoposide, 5-fluorouracil, cyclophosphamide and mixtures thereof, said compound and said principal drug being administered sufficiently contemporaneously such that said cancer is exposed to said compound and said principal drug simultaneously, the ratio at which said compound to said principal drug is administered being from about 0.04 to about 170.

74. The method of claim 72 in which $R_2$ in said compound (1) is $CH_3$ and $R_3$ is $CH_3$.

75. The method of claim 72 in which $R_2$ in said compound (1) is $C_2H_5$ and $R_3$ is $CH_3$.

76. A pharmaceutical composition for reducing drug resistant uterine, ovarian, breast, lymphoma, cartilage/bone, leukemia, liver, abdominal area, lung, cervical, pelvic, adrenal gland, iliac, Hodgkin's disease an thyroid cancers in a patient comprising:

a combination of (1) a compound having the formula:

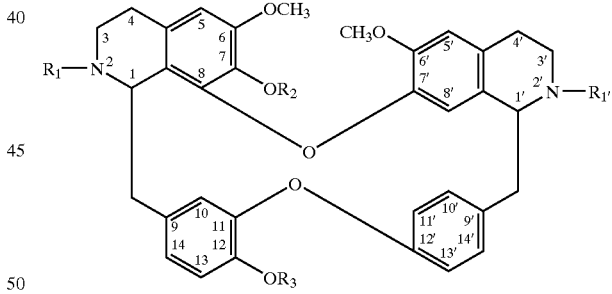

where $R_1$ and $R_1'$ are the same or different short chained carbon based moieties; $R_2$ is $CH_3$ or $C_2H_5$ and $R_3$ is $CH_3$ or Hydrogen, and the isomeric configuration at the C-1' chiral carbon location is "S", and (2) at least one principal drug known to be effective for treating whichever of said cancers is being treated, said principal drug being one of doxorubicin, vincristine, vinblastine, taxol, etoposide, 5-fluroruracil, cyclophosphamide and mixtures thereof, the ratio of said compound to said principal drug being from about 0.04 to about 170.

77. The pharmaceutical composition of claim 76 in which $R_2$ in said compound (1) is $CH_3$ and $R_3$ is $CH_3$.

78. The pharmaceutical composition of claim 76 in which $R_2$ in said compound (1) is $C_2H_5$ and $R_3$ is $CH_3$.

79. A pharmaceutical kit for treating and thereby reducing drug resistant uterine, ovarian, breast, lymphoma, cartilage/bone, leukemia, liver, abdominal area, lung, cervical, pelvic, adrenal gland, iliac, Hodgkin's disease and thyroid cancers in a patient comprising:

a multidrug resistant reverser compound having the formula:

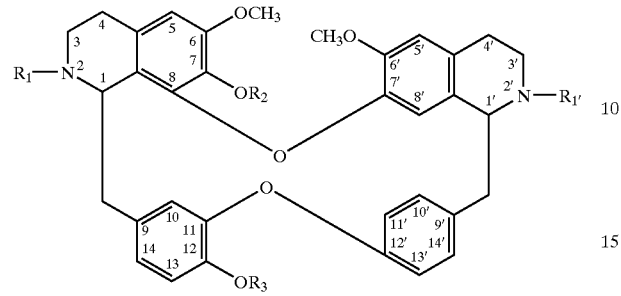

where $R_1$ and $R_1'$ are the same or different short chained carbon based moieties; $R_2$ is $CH_3$ or $C_2H_5$ and $R_3$ is $CH_3$ or Hydrogen, and the isomeric configuration at the C-1' chiral carbon location is "S", and (2) at least one principal drug known to be effective for treating whichever of said cancers is being treated, said principal drug being one of doxorubicin, vincristine, vinblastine, taxol, etoposide, 5-fluorouracil, cyclophosphamide and mixtures thereof, the ratio of said compound to said principal drug being from about 0.04 to about 170.

80. The pharmaceutical kit of claim 79 in which $R_2$ in said compound (1) is $CH_3$ and $R_3$ is $CH_3$.

81. The pharmaceutical kit of claim 79 in which $R_2$ in said compound (1) is $C_2H_5$ and $R_3$ is $CH_3$.

* * * * *

UNITED STATES PATENT AND TRADEMARK OFFICE
CERTIFICATE OF CORRECTION

PATENT NO. : 6,911,454 B1
APPLICATION NO. : 08/293745
DATED : June 28, 2005
INVENTOR(S) : Knox Van Dyke It is certified that error appears in the above-identified patent and that said Letters Patent is hereby corrected as shown below:

Column 1:
Line 31, "disease" should be --diseases--.

Column 2:
Line 12, "in vitro" should be --*in vitro*--.
Line 13, "in vivo" should be --*in vivo*--.
Line 22, "in vitro" should be --*in vitro*--.
Line 23, "in vivo" should be --*in vivo*--.
Line 24, "in vitro" should be --*in vitro*--.
Line 31, "have" should be --has--.
Line 58, "ab initio" should be -- *ab initio*--.

Column 3:
Line 61, "cancel" should be --cancer--.

Column 5:
Line 4, "in vivo" should be --*in vivo*--.
Line 9, "in vitro;" should be -- *in vitro*--.
Line 11, "in vivo" should be --*in vivo*--.
Line 41, "regime" should be --regimen--.

Column 6:
Line 22, After "concentration of" insert --reverser makes it possible to use a lower concentration of --.
Line 23, "in vivo" should be --*in vivo*--.
Line 67, "In vitro" should be --*In vitro*--.

Column 7:
Line 4, "in vivo" should be --*in vivo*--.
Line 20, "grown" should be --grow--.
Line 49, "24 well" should be --24-well--.

Column 8:
Line 52, "the" should be --The--.

Column 9:
Line 7, "regime" should be --regimen--.
Line 54, "cancel" should be --cancer--.
Line 66, "in vitro and in vivo" should be --*in vitro* and *in vivo*--.

UNITED STATES PATENT AND TRADEMARK OFFICE
CERTIFICATE OF CORRECTION

PATENT NO. : 6,911,454 B1
APPLICATION NO. : 08/293745
DATED : June 28, 2005
INVENTOR(S) : Knox Van Dyke It is certified that error appears in the above-identified patent and that said Letters Patent is hereby corrected as shown below:

Column 10:
Line 3, "in vitro" should be -- *in vitro*--.
Line 60, "in vitro studies, in vivo" should be --*in vitro* studies, *in vivo*--.

Column 12:
Line 21, "Van Kyke" should be --Van Dyke--.

Column 15:
Line 21, "IN VITRO" should be --*IN VITRO*--.
Line 31, "TA" should be -- FA --.

Column 16:
Line 52, "in vivo" should be --*in vivo*--.

Column 17:
Line 19, "claim 67" should be --claim 2--.
Line 21, "claim 67" should be --claim 2--.
Line 23, "claim 67" should be --claim 2--.

Column 19:
Line 47, "claim 31" should be --claim 35--.
Line 53, "claim 31" should be -- claim 35--.
Line 57, "claim 31" should be --claim 37--.
Line 59, "claim 31" should be --claim 37--.
Line 64, "in vivo" should be --*in vivo*--.

Column 20:
Line 37, "claim 44" should be --claim 45--.

Column 21:
Line 17, "in vivo" should be --*in vivo*--.

UNITED STATES PATENT AND TRADEMARK OFFICE
CERTIFICATE OF CORRECTION

PATENT NO. : 6,911,454 B1
APPLICATION NO. : 08/293745
DATED : June 28, 2005
INVENTOR(S) : Knox Van Dyke It is certified that error appears in the above-identified patent and that said Letters Patent is hereby corrected as shown below:

Column 22:
Line 1, "in vivo" should be --*in vivo*--.
Line 29 "claim 72" should be --claim 73--.
Line 31, "claim 72" should be --claim 73--.
Line 36, "an" should be --and--.

Signed and Sealed this

First Day of May, 2007

JON W. DUDAS
*Director of the United States Patent and Trademark Office*